(12) United States Patent
Park et al.

(10) Patent No.: US 12,102,951 B2
(45) Date of Patent: Oct. 1, 2024

(54) AIR CLEANER

(71) Applicant: LG Electronics Inc., Seoul (KR)

(72) Inventors: Sangjin Park, Seoul (KR); Dooyeong Kwak, Seoul (KR); Naehyun Park, Seoul (KR)

(73) Assignee: LG Electronics Inc., Seoul (KR)

(*) Notice: Subject to any disclaimer, the term of this patent is extended or adjusted under 35 U.S.C. 154(b) by 535 days.

(21) Appl. No.: 17/547,781

(22) Filed: Dec. 10, 2021

(65) Prior Publication Data
US 2022/0184540 A1 Jun. 16, 2022

(30) Foreign Application Priority Data

Dec. 11, 2020 (KR) .................. 10-2020-0173583
Jan. 4, 2021 (KR) .................. 10-2021-0000532

(51) Int. Cl.
B01D 46/00 (2022.01)
A61L 9/20 (2006.01)
(Continued)

(52) U.S. Cl.
CPC ............ *B01D 46/0028* (2013.01); *A61L 9/20* (2013.01); *B01D 46/0005* (2013.01);
(Continued)

(58) Field of Classification Search
CPC .... B01D 46/42; B01D 29/56; B01D 46/0002; B01D 46/0005; B01D 46/0021;
(Continued)

(56) References Cited

U.S. PATENT DOCUMENTS 3,804,942 A 4/1974 Wakamatsu et al.
6,680,028 B1 * 1/2004 Harris .................. F24F 1/0071
96/132
(Continued)

FOREIGN PATENT DOCUMENTS

CN 107642844 1/2018
CN 207230744 4/2018
(Continued)

OTHER PUBLICATIONS

Extended European Search Report in European Application No. 21213168.4, dated Apr. 25, 2022, 7 pages.
(Continued)

*Primary Examiner* — Minh Chau T Pham
(74) *Attorney, Agent, or Firm* — Fish & Richardson P.C.

(57) ABSTRACT

An air cleaner includes: a housing including a suction portion suctioning air and a discharge portion discharging air, a frame disposed inside the housing, a sterilizer sterilizing the suctioned air, a filter assembly filtering air, a blower moving air, a flow converter disposed on a top surface of the housing, guiding a flow of air, and discharging air inside the housing to an outside, and a guide guiding a direction of the flow converter. The sterilizer includes a sterilizing light source generating sterilizing light, a first sterilizing casing accommodating the sterilizing light source, and a second sterilizing casing coupled to a lower portion of the first sterilizing casing and supporting the first sterilizing casing and the sterilizing light source, where a portion of the first sterilizing casing is spaced apart from the second sterilizing casing to define a space therebetween that dissipates heat generated from the sterilizing light source.

20 Claims, 17 Drawing Sheets

(51) Int. Cl.
  *B01D 46/66* (2022.01)
  *F24F 8/108* (2021.01)
  *F24F 8/20* (2021.01)
  *F24F 8/22* (2021.01)

(52) U.S. Cl.
  CPC ......... *B01D 46/0049* (2013.01); *B01D 46/66* (2022.01); *A61L 2209/12* (2013.01); *A61L 2209/14* (2013.01); *B01D 46/0038* (2013.01); *B01D 2279/65* (2013.01)

(58) Field of Classification Search
  CPC ...... F24F 11/89; F24F 8/80; F24F 8/22; F24F 2013/205; F24F 2221/12; A61L 9/20
  USPC .............. 55/358, 471–473; 422/121; 96/222
  See application file for complete search history.

(56) References Cited

U.S. PATENT DOCUMENTS

| | | | | |
|---|---|---|---|---|
| 10,323,855 | B2* | 6/2019 | Jung | F24F 8/10 |
| 2022/0023789 | A1* | 1/2022 | Oh | F24F 13/10 |
| 2022/0026085 | A1* | 1/2022 | Kim | F24F 8/80 |
| 2023/0175721 | A1* | 6/2023 | Kim | F24F 13/28 |
| | | | | 55/471 |

FOREIGN PATENT DOCUMENTS

| | | |
|---|---|---|
| CN | 111457490 | 7/2020 |
| EP | 3211336 | 8/2017 |
| EP | 3211347 | 8/2017 |
| JP | S51-017887 | 2/1976 |
| JP | S51-017888 | 2/1976 |
| JP | H11-047255 | 2/1999 |
| JP | 2019509171 | 4/2019 |
| JP | 2020-171739 | 10/2020 |
| KR | 20160015084 | 2/2016 |
| KR | 10-1809370 | 12/2017 |
| KR | 20200011814 | 2/2020 |
| KR | 10-2020- 0029233 | 3/2020 |
| KR | 20200044333 | 4/2020 |
| KR | 20200135261 | 12/2020 |

OTHER PUBLICATIONS

Office Action in Japanese Application No. 2021-199061, dated Oct. 11, 2022, 8 pages (with English translation).
Notice of Allowance in Chinese Appln. No. 202111515754.7, mailed on May 12, 2023, 16 pages (with English translation).
Notice of Allowance in Japanese Appln. No. 2021-199061, dated Aug. 8, 2023, 8 pages (with English translation).

* cited by examiner

AIR CLEANER

CROSS-REFERENCE TO RELATED APPLICATIONS

This application claims the benefit of Korean Patent Application Nos. 10-2020-0173583, filed on Dec. 11, 2020, and 10-2021-0000532, filed on Jan. 4, 2021, the disclosures of which are incorporated by reference in their entirety.

TECHNICAL FIELD

The present disclosure relates to an air cleaner.

BACKGROUND

An air cleaner is understood as an apparatus that suctions and filters polluted air and then discharges filtered air, and is constructed to purify an indoor space such as a home or office. In general, the air cleaner includes a blower constructed to suction external air and discharge air, and a filter disposed inside the blower to filter dust, bacteria, or the like in the air. In this structure, the air cleaner may further include a flow converter constructed to adjust a discharge direction of the air discharged from the blower.

In recent years, beyond an indoor air cleaner used in a large space such as the home or the office, a portable air cleaner in a small and light form for easy portability has been developed to purify air in a narrow space such as a studio or an interior of a vehicle. Such portable air cleaner may be understood as an apparatus suitable for a user who has a life pattern of going out or moving to several places rather than staying for a long time in one place such as the home or the office, and may have an advantage of being easily carried and easily used by the user at a desired place.

In the portable air cleaner, a filter for physical particles such as the dust, a filter for a chemical substance such as gas, a filter for microorganisms such as the bacteria and viruses, and the like may be used in combination. In addition to this, a UVC sterilizer for sterilizing the filter may be further included.

In some implementations, the UVC sterilizer may be constructed to irradiate UVC light using a UVC LED. Because such UCV light may have a harmful effect on a human body, it is necessary to prevent the UCV light from leaking to the outside of the air cleaner. In addition, when the UVC light is irradiated, heat may be generated from the UVC LED, which may shorten a lifespan of the air cleaner or may induce a failure of the air cleaner, so that there is a need for a method for dissipate the heat.

SUMMARY

The present disclosure is directed to an air cleaner capable of effectively dissipating heat generated when irradiating sterilizing light to the outside, including a sterilizer having a plurality of discharge portions.

The present disclosure is also directed to an air cleaner capable of blocking a light leakage phenomenon in which sterilizing light leaks to the outside through a sterilizing casing having a non-flat top surface.

According to one aspect of the subject matter described in this application, an air cleaner can include a housing including a suction portion configured to suction air from an outside of the housing and a discharge portion configured to discharge air from the housing, a frame disposed inside the housing, a sterilizer disposed inside the frame and configured to sterilize the suctioned air, a filter assembly disposed in the frame and configured to filter air inside the housing, a blower disposed inside the frame and configured to move air inside the housing, a flow converter that is disposed on a top surface of the housing and that is configured to guide a flow of air inside the housing and discharge air inside the housing to an outside of the housing, and a guide configured to guide a direction of the flow converter. The sterilizer can include a sterilizing light source configured to generate sterilizing light, a first sterilizing casing configured to accommodate the sterilizing light source, and a second sterilizing casing that is coupled to a lower portion of the first sterilizing casing and that supports the first sterilizing casing and the sterilizing light source, where a portion of the first sterilizing casing is spaced apart from the second sterilizing casing to define a space therebetween that is configured to dissipate heat generated from the sterilizing light source.

Implementations according to this aspect can include one or more of the following features. For example, the sterilizer can further include a main discharge portion that defines an opening at a central portion of a top surface of the first sterilizing casing to irradiate the sterilizing light generated by the sterilizing light source, a first discharge portion that defines an opening at the top surface of the first sterilizing casing to dissipate the heat generated from the sterilizing light source, and a second discharge portion that defines an opening at a sidewall of the first sterilizing casing to dissipate the heat generated from the sterilizing light source.

In some implementations, a portion of the suction portion can overlap the second discharge portion. In some examples, the frame can include an air inlet that defines an opening at a sidewall of the frame and that is in fluid communication with the suction portion, and the suction portion, the air inlet, and the second discharge portion can be in fluid communication with each other.

In some implementations, the first sterilizing casing can include a protrusion protruding from the sidewall of the first sterilizing casing toward the second sterilizing casing, the second sterilizing casing can include a coupling groove defined at a position corresponding to the protrusion, and the first sterilizing casing and the second sterilizing casing can be coupled to each other by fastening between the protrusion and the coupling groove. In some examples, the protrusion and the coupling groove can include a plurality of protrusions and a plurality of coupling grooves, respectively, and a number of the plurality of protrusions can be equal to a number of the plurality of coupling grooves.

In some examples, the protrusion can include a first protrusion that includes a first set of protrusions and a second protrusion that includes a second set of protrusions, and the first protrusion and the second protrusion can have different extension lengths. In some examples, an extension length of the first protrusion can be greater than an extension length of the second protrusion, and each of the second set of protrusions can be disposed on each of both sides of the first set of protrusions, respectively.

In some implementations, the protrusion can further include a third protrusion protruding from the top surface of the first sterilizing casing toward the second sterilizing casing, and the first sterilizing casing and the sterilizing light source can be coupled to each other by the third protrusion. In some implementations, the first protrusion can pass through the coupling groove to couple the coupling groove, and the second protrusion can be in contact with a portion of a top surface of the second sterilizing casing adjacent to the coupling groove.

In some implementations, the sterilizer can further include a third discharge portion that is disposed between the first protrusion and the second protrusion and that recesses in a direction away from the second sterilizing casing to dissipate the heat generated from the sterilizing light source. In some implementations, the air cleaner can further include a battery that is disposed inside the second sterilizing casing and that is configured to supply power, where the sterilizing light source and the battery can be electrically connected to each other by a harness.

In some examples, one of the plurality of coupling grooves can have an area greater than an area of each of the remaining coupling grooves, and the harness can extend through the at least one coupling groove. In some examples, a protrusion corresponding to the at least one coupling groove among the plurality of protrusions can protrude farther in a circumferential direction of the first sterilizing casing than the remaining protrusions.

In some implementations, the top surface of the first sterilizing casing can have a concave shape. In some examples, the top surface of the first sterilizing casing can have a downward slope toward a top surface of the second sterilizing casing from an edge portion to the central portion of the top surface of the first sterilizing casing.

In some examples, the first discharge portion can include a plurality of through-holes having different extension lengths extending in a circumferential direction of the top surface of the first sterilizing casing. In some examples, the first discharge portion can include a first through-hole, a second through-hole, and a third through-hole, and an extension length of the third through-hole can be greater than an extension length of the second through-hole, and the extension length of the second through-hole can be greater than an extension length of the first through-hole, where the extension length of each of the first through-hole, the second through-hole, and the third through-hole extends in the circumferential direction of the top surface of the first sterilizing casing.

In some implementations, the first discharge portion can further include a fourth through-hole having an extension length less than the first through-hole. In some examples, each of the first through-hole, the second through-hole, the third through-hole, and the fourth through-hole can include a plurality of through-holes.

DETAILED DESCRIPTION

Hereinafter, an overall configuration of an exemplary air cleaner 1 will be described with reference to FIGS. 1 to 3.

Figure 1:
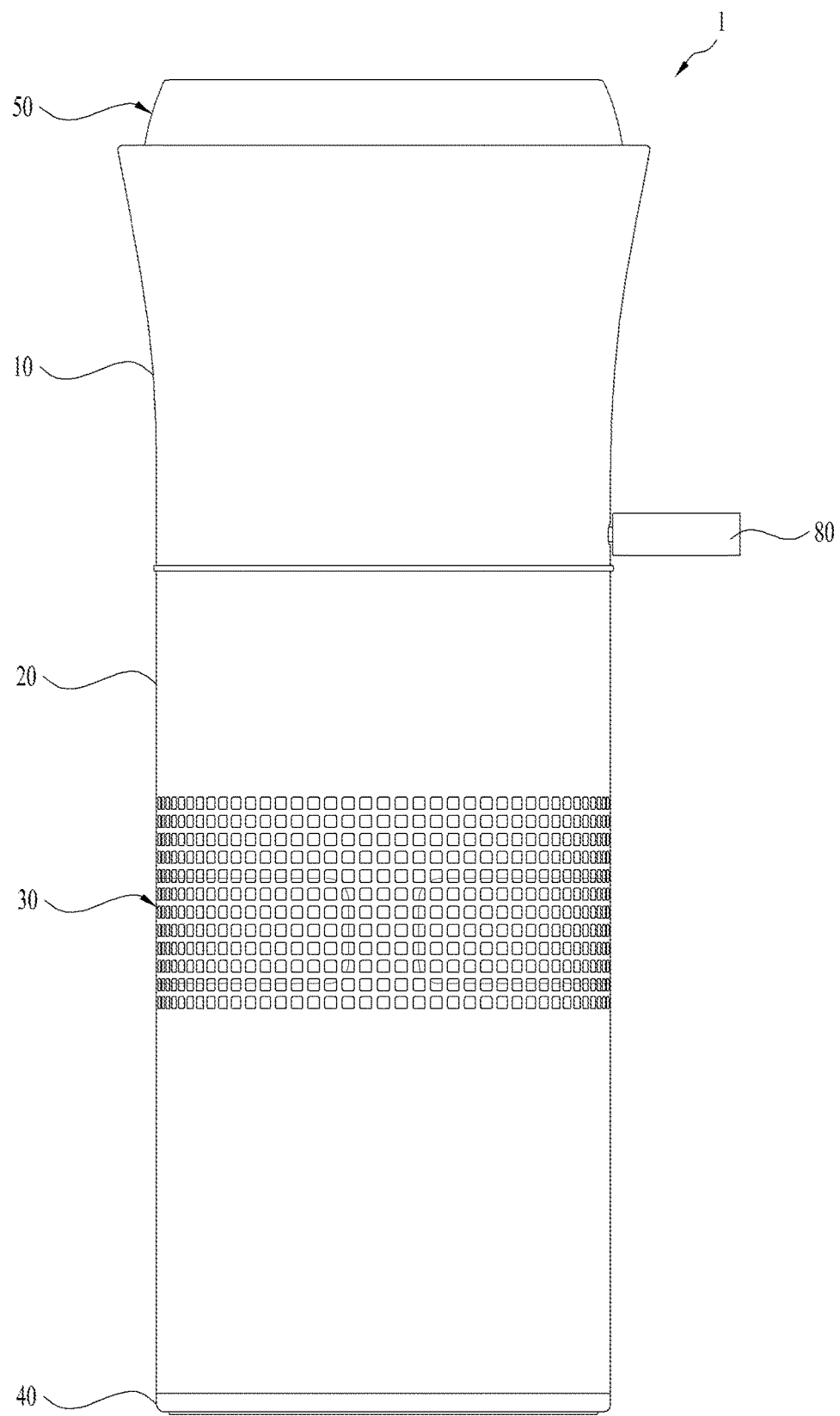
FIG. 1 is a diagram illustrating an exemplary air cleaner.
Figure 2:
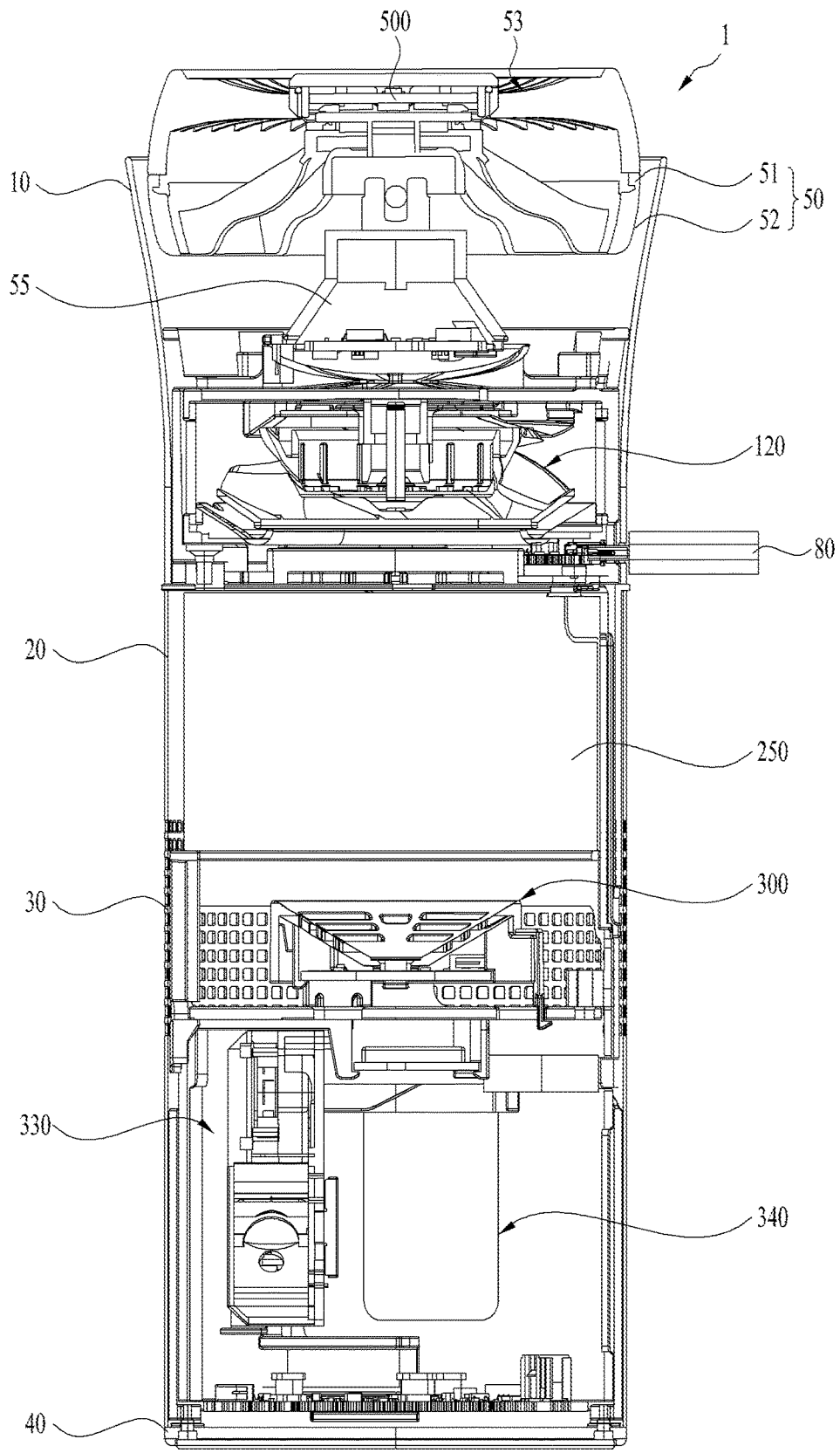
FIG. 2 is a diagram illustrating a cross-sectional view of the exemplary air cleaner of FIG. 1.
Figure 3:
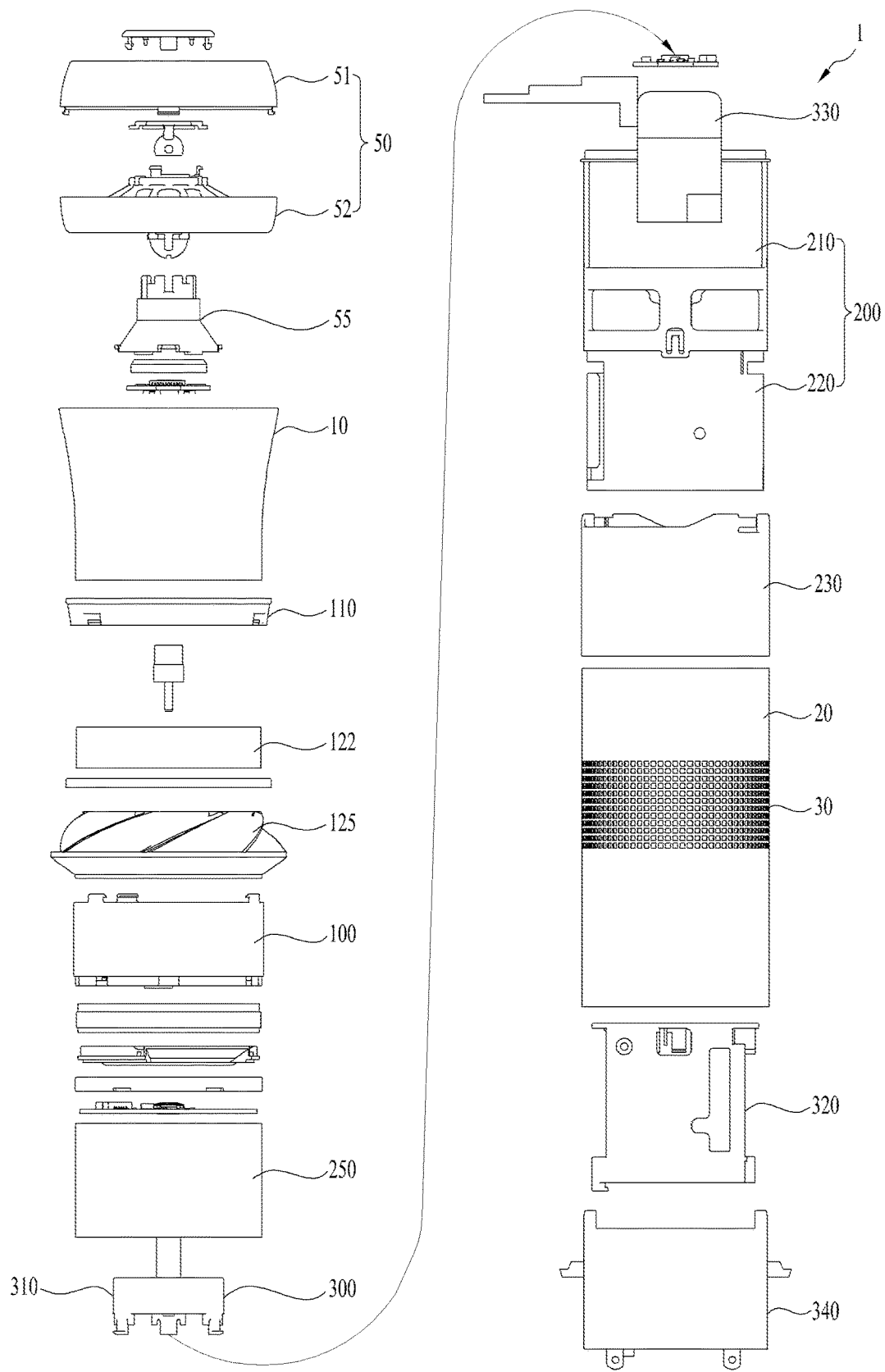
FIG. 3 is a diagram illustrating an exploded perspective view of an exemplary air cleaner.

FIG. 1 is a diagram illustrating the exemplary air cleaner 1, FIG. 2 is a diagram illustrating a cross-sectional view of the exemplary air cleaner 1 of FIG. 1, and FIG. 3 is a diagram illustrating an exploded perspective view of the exemplary air cleaner 1.

The air cleaner 1 can include a housing 10 and 20, a blower 120 that provides an airflow inside the housing 10 and 20, a filter assembly 250 that purifies air flowing inside the housing 10 and 20, and a flow converter 50 that discharges purified air.

The air cleaner 1 can further include a sterilizer 300 for removing foreign substances contained in the air flowing inside the housing 10 and 20 or for sterilizing the filter assembly 250, a dust sensor assembly 330 that senses or detects dust contained in the suctioned air, and a battery 340 that supplies power to a controller disposed inside the housing 10 and 20.

The controller can include at least one PCB and one or more components that will be described later.

The housing 10 and 20 defines a space for accommodating internal components and a portion of an exterior of the air cleaner 1. The housing 10 and 20 can have any shapes capable of providing the above-described space. In some implementations, the housing 10 and 20 can include a first housing 10 defining an upper portion and a second housing 20 defining a lower portion, and the first housing 10 and the second housing 20 together can have a hollow cylindrical shape.

The blower 120, the filter assembly 250, the flow converter 50, the sterilizer 300, the dust sensor assembly 330, and the battery 340 can be disposed inside the housing 10 and 20.

The housing 10 and 20 can include a suction portion 30 that is in fluid communication with an exterior and an interior of the housing 10 and 20. For example, the suction portion 30 defines an opening at the housing 10 and 20, and can be provided at a position that is spaced apart from an upper end and a lower end of the housing 10 and 20. In some implementations, the suction portion 30 can be disposed in the second housing 20 and may not be disposed in the first housing 10. In some implementations, the suction portion 30 can be provided at a position that is spaced apart from upper and lower ends of the second housing 20.

In some implementations, the housing 10 and 20 can further include a discharge portion that is in fluid communication with the exterior and the interior of the housing 10 and 20. The discharge portion can define an opening at the housing 10 and 20, and can be provided at the upper end of the housing 10 and 20. In some implementations, the discharge portion can be disposed in the first housing 10 and may not be disposed in the second housing 20. In some implementations, the discharge portion can be provided at an upper end of the first housing 10, for example, between the first housing 10 and the flow converter 50.

In some implementations, the suction portion 30 can have a shape of a grill that defines an opening at a sidewall of the second housing 20, and the discharge portion can define an opening at a top surface of the first housing 10.

The flow converter 50 can be provided to be in fluid communication with the discharge portion at the upper end of the first housing 10, and a portion of the flow converter 50 can be detachably coupled to the first housing 10. The flow converter 50 can include a discharge grill 53 that guides the air located inside the housing 10 and 20 to the outside of the housing 10 and 20.

The flow converter 50 can be located above the suction portion 30. For example, when the blower 120 provides the airflow, the air located outside the housing 10 and 20 can be introduced into the housing 10 and 20 through the suction portion 30 and then discharged to the outside of the housing 10 and 20 through the discharge portion and the discharge grill 53.

The housing 10 and 20 can include a frame 100 and 200 that is disposed below the flow converter 50 and that accommodates the blower 120, the filter assembly 250, the sterilizer 300, the dust sensor assembly 330, and the battery 340 therein.

In some implementations, the frame 100 and 200 can include a first frame 100 that defines an upper portion and that accommodates the blower 120 therein, and a second frame 200 that defines a lower portion and that accommodates the filter assembly 250, the sterilizer 300, the dust sensor assembly 330, and the battery 340 therein, and the first frame 100 and the second frame 200 can have a hollow cylindrical shape together.

A guide support frame 110 can be coupled to a top surface of the first frame 100, and a guide 55 that guides a direction of the flow converter 50 can be seated on and coupled to a portion of a top surface of the guide support frame 110.

The filter assembly 250 and the sterilizer 300 can be sequentially stacked inside the second frame 200. For example, the filter assembly 250 can be stacked on the sterilizer 300 inside the second frame 200.

The filter assembly 250 can include a filter capable of removing the foreign substances contained in the air. For example, the filter can include various filters corresponding to a type of the foreign substances to be removed. By way of further example, the filter can include at least one of a dust filter that removes the dust in the air, a biochemical filter that removes organisms such as mites in the air, and a deodorizing filter that removes substances that cause odors (e.g., hydrogen sulfide, methyl mercaptan, trimethylamine, and the like).

The filter assembly 250 can be detachably coupled to the interior of housing 10 and 20.

In some implementations, the filter assembly 250 can be located above the suction portion 30 and below the flow converter 50. For example, the air flowing from the suction portion 30 toward the discharge grill 53 can be purified by the filter assembly 250.

In some implementations, the filter assembly 250 can be disposed above the suction portion 30 and below the blower 120. The filter assembly is disposed above the blower 120 because a flow speed of the air flow provided by the blower 120 can be reduced by the filter assembly 250 if the filter assembly 250 is located above the blower 120.

The sterilizer 300 can remove the microorganisms contained in the air or fungi remaining in the filter assembly 250, and can be disposed below the filter assembly 250. For example, the sterilizer 300 is disposed below the filter assembly 250 to remove the microorganisms included in the air before the microorganisms flow into the filter assembly 250 and to remove the microorganisms located in the filter assembly 250.

The sterilizer 300 can be disposed at a vertical level to overlap with the suction portion 30. For example, the sterilizer 300 and the suction portion 30 can overlap in a vertical direction. In some implementations, the sterilizer 300 can first sterilize the microorganisms contained in the air flowed into the housing 10 and 20 through the suction portion 30.

The battery 340 can be disposed below the blower 120, the filter assembly 250, the flow converter 50, and the sterilizer 300. For example, the battery 340 can be disposed inside the housing 10 and 20 and at the lower end of the housing 10 and 20.

The battery 340 can be disposed inside the housing 10 and 20 and at the lower end of the housing 10 and 20 because of its large weight relative to the same volume (a high density). Further, this is because the battery 340 can be stably implemented in a specific place after moving the air cleaner 1.

In some implementations, the battery 340 can be disposed below the suction portion 30. For example, the air flowed through the suction portion 30 can flow upward toward the flow converter 50, so that the air may not pass through the battery 340. When the air cleaner 1 is portable, a strength of the airflow provided by the blower 120 can be restricted. As the battery 340 is positioned below the suction portion 30, a volume of a space controlled by the blower 120 may be reduced.

Accordingly, the air flowed into the housing 10 and 20 through the suction portion 30 can flow to the filter assembly 250 after being sterilized by the sterilizer 300. The air purified through the filter assembly 250 can pass through the blower 120 and flow from the interior of the housing 10 and 20 to the exterior of the housing 10 and 20 through the discharge grill 53.

Hereinafter, the housing 10 and 20 will be described with reference to FIGS. 1 to 4 and FIG. 8.

Figure 4:
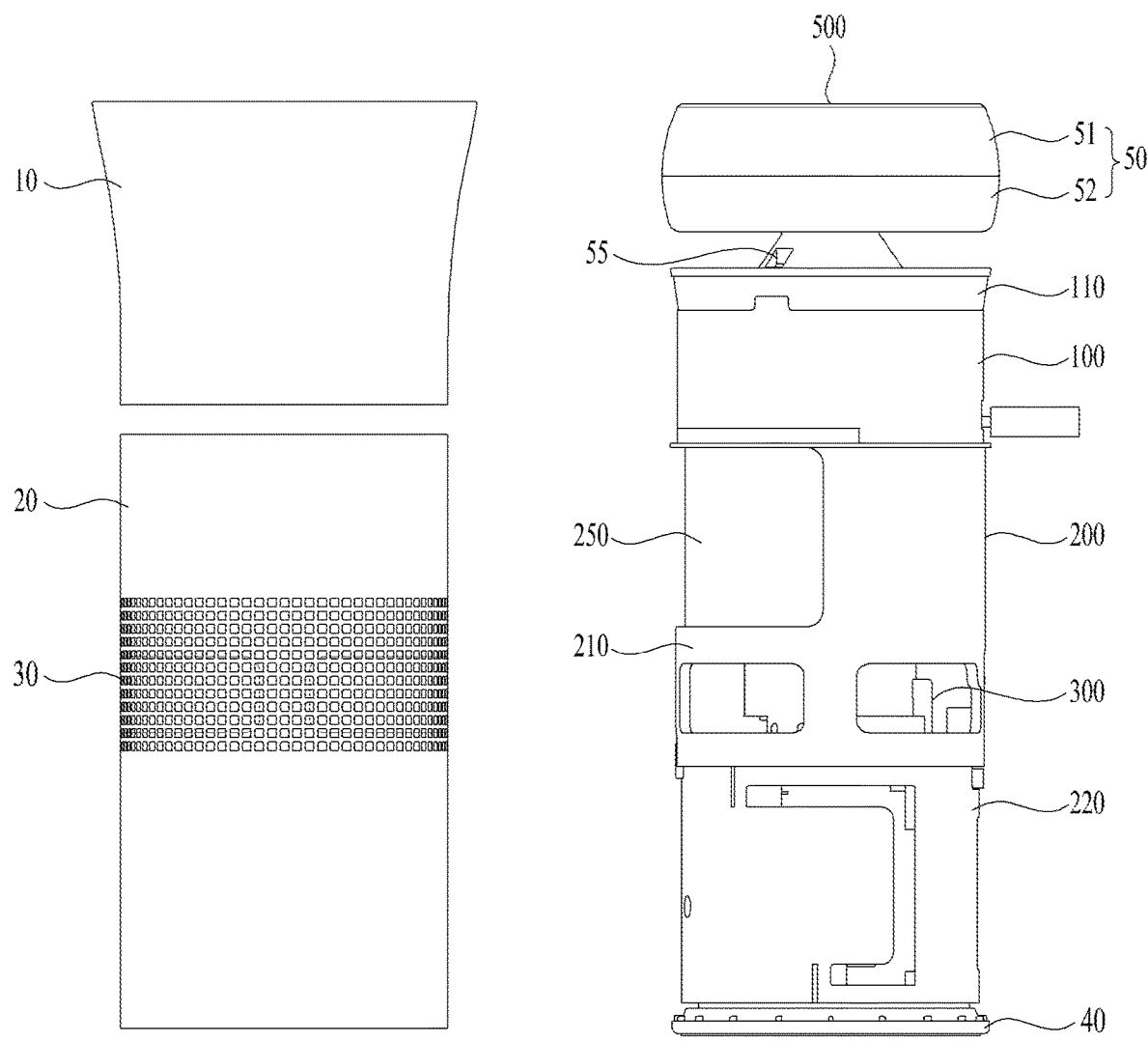
FIG. 4 is a diagram illustrating examples of a housing and a frame.
Figure 8:
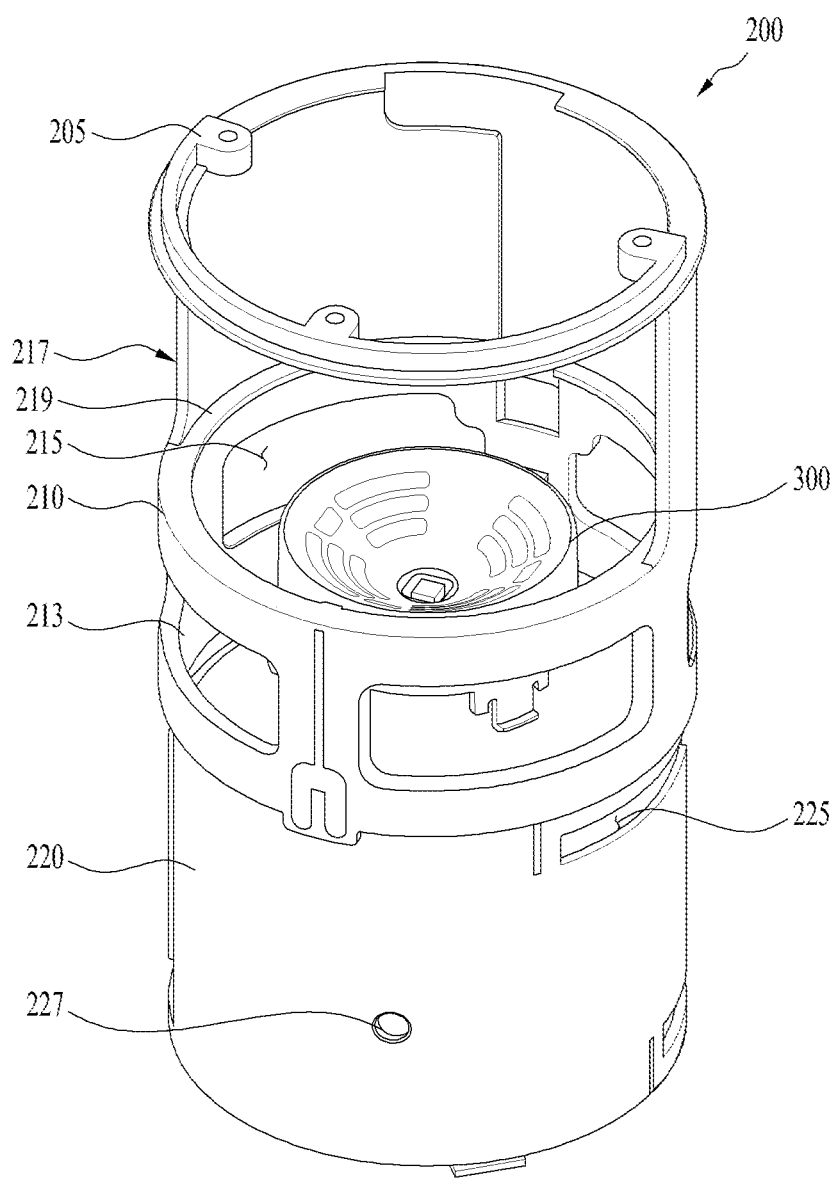
FIG. 8 is a diagram illustrating examples of a second frame and a sterilizer.

FIG. 4 is a diagram illustrating examples of the housing 10 and 20 and the frame 100 and 200, and FIG. 8 is a diagram illustrating examples of the second frame 200 and the sterilizer 300.

Referring to FIGS. 1 to 4 and FIG. 8, the housing 10 and 20 can include the first housing 10 and the second housing 20 that define the exterior and respectively define the upper and lower portions of the air cleaner 1, and the frame 100 and 200 can include the first frame 100 covered by the first housing 10 and the second frame 200 covered by the second housing 20.

In some implementations, the second frame 200 can include a second upper frame 210 defining an upper portion and a second lower frame 220 defining a lower portion. The second upper frame 210 and the second lower frame 220 can be integrally provided to define the second frame 200, but the present disclosure may not be necessarily limited thereto. For example, the second upper frame 210 and the second lower frame 220 can be provided separately, and a lower portion of the second upper frame 210 and an upper portion of the second lower frame 220 can be coupled to each other to define the second frame 200.

In some implementations, the filter assembly 250 and the sterilizer 300 can be accommodated in the second upper frame 210, and the dust sensor assembly 330 and the battery 340 can be accommodated in the second lower frame 220.

A portion of the blower 120 and the flow converter 50 can be accommodated in the first frame 100, and the dust sensor assembly 330, the battery 340, the sterilizer 300, and the filter assembly 250 can be accommodated in the second frame 200. In some implementations, the first frame 100 can accommodate the guide 55 that is disposed between the blower 120 and the flow converter 50 and that is configured to guide a state change of the flow converter 50, and the guide support frame 110 for supporting the guide 55.

The first housing 10 can be provided to be movable or detachable relative to the second housing 20. For example, the first housing 10 can be detachably coupled to the second housing 20. Accordingly, a user may periodically replace the filter assembly 250. In some implementations, when the first housing 10 and the second housing 20 are separated from each other, the filter assembly 250 may be exposed to the user.

The second housing 20 can have a hollow cylindrical shape. The suction portion 30 can be disposed at the position that is spaced apart from the lower end of the second housing 20. In some implementations, the air cleaner 1 is disposed in a vehicle. For example, a smoother air flow can be provided when the air cleaner 1 is erected in a component like a cup holder of the vehicle.

In some implementations, the suction portion 30 can have a shape of the grill having one or more openings at the sidewall of the second housing 20 at the position that is spaced apart from the lower end of the second housing 20.

The suction portion 30 is sufficient to provide the features described above as long as it has a shape that is in fluid communication with the exterior and the interior of the second housing 20. In some implementations, the suction portion 30 can include a plurality of through-holes. For example, each of the plurality of through-holes can have a rectangular shape.

In some implementations, the first housing 10 can have a shape that does not interfere with the movement of the flow converter 50 to accommodate the flow converter 50 that is movable. For example, the first housing 10 can have a hollow cylindrical shape connected to the upper end of the second housing 20.

A portion of the flow converter 50 can be accommodated in an upper portion of the first housing 10 and can be movable. A portion of the blower 120 can be accommodated in a lower portion of the first housing 10. Accordingly, the air passed through the blower 120 can be discharged to the outside of the housing 10 and 20 through the discharge grill 53 provided to be movable.

The first frame 100 can have a height less than a height of the first housing 10, and the second frame 200 can have a height corresponding to a height of the second housing 20.

The battery 340, the dust sensor assembly 330, the sterilizer 300, and the filter assembly 250 can be accommodated in the second frame 200. In some implementations, the first frame 100 that accommodates the blower 120 therein can be coupled to the top surface of the second frame 200.

The second frame 200 can include a dust sensor assembly accommodating portion and a battery accommodating portion that are disposed at a lower portion of the second frame 200 and that respectively accommodate the dust sensor assembly 330 and the battery 340 therein, and can include a filter assembly detachable portion 215 that is disposed in an upper portion of the second frame 200 and detachably accommodates the filter assembly 250 therein, and a sterilization fastening portion disposed between the filter assembly detachable portion 215 and the battery accommodating portion to accommodate the sterilizer 300 therein. In addition, the second frame 200 can further include a frame fastening portion 205 disposed in the upper portion of the second frame 200 to fix the first frame 100 to the second frame 200.

In some examples, "accommodating" may refer to being provided at a vertical level to overlap with a component to be accommodated.

The battery accommodating portion can be disposed at the lower portion of the second frame 200. The frame fastening portion 205 can be disposed at the upper portion of the second frame 200. The filter assembly detachable portion 215 can be disposed between the battery accommodating portion and the frame fastening portion 205.

In some implementations, the housing 10 and 20 can further include an inner housing 230 for moving the second frame 200 with respect to the second housing 20.

The inner housing 230 can be coupled to an inner circumferential surface of the second housing 20, and can be detachably coupled to an outer circumferential surface of the second frame 200. For example, the inner housing 230 can be coupled to the inner circumferential surface of the second housing 20, and can be detachably coupled to an outer circumferential surface of the battery accommodating portion.

Accordingly, the second frame 200 can be provided to be detachable with respect to the second housing 20. For example, after separating the first housing 10 and the second housing 20 from each other to replace the filter assembly 250, the user may detach the second frame 200 from the second housing 20.

In some implementations, the second frame 200 can move upward relative to the second housing 20. For example, the second housing 20 can move downward relative to the second frame 200.

This structure can expose the filter assembly 250 to the user when the first housing 10 and the second housing 20 are separated from each other.

The second frame 200 can further include an air inlet 213 that is in fluid communication with the suction portion 30. For example, the air inlet 213 can be defined through a portion of the sidewall of the second frame 200. Accordingly, the air suctioned by the suction portion 30 can be introduced into the sterilizer 300 after passing through the air inlet 213.

The air inlet 213 can overlap with the suction portion 30 partially. A predetermined height of the suction portion 30 can be greater than a height of the air inlet 213.

Accordingly, the air flowed through the suction portion 30 can flow through the air inlet 213, and the air passed through the air inlet 213 can be sterilized by the sterilizer 300.

The air inlet 213 is sufficient to provide the features described above as long as it has a shape that is in fluid communication with the interior and the exterior of the second frame 200. In some implementations, the air inlet 213 can have a rectangular shape and can include a plurality of air inlets spaced apart from each other in a circumferential direction.

The filter assembly detachable portion 215 can include a filter assembly opening 217 that is an opening defined above the air inlet 213 to provide a space in which the filter assembly 250 can move, and a filter assembly fixing rib 219 that couples the filter assembly 250 disposed inside the filter assembly detachable portion 215 through the filter assembly opening 217.

The filter assembly opening 217 can have a shape corresponding to a shape of the filter assembly 250.

The filter assembly fixing rib 219 can protrude from an inner circumferential surface of the second frame 200 to couple the filter assembly 250 inserted into the second frame 200. For example, the filter assembly fixing rib 219 can protrude inwardly of the second frame 200 from a lower end of the filter assembly opening 217.

The frame fastening portion 205 can be disposed at an upper end of the second frame 200 to couple the first frame 100 that accommodates the blower 120 to the second frame 200.

Hereinafter, the exemplary blower 120 will be described with reference to FIGS. 4 to 6.

Figure 5:
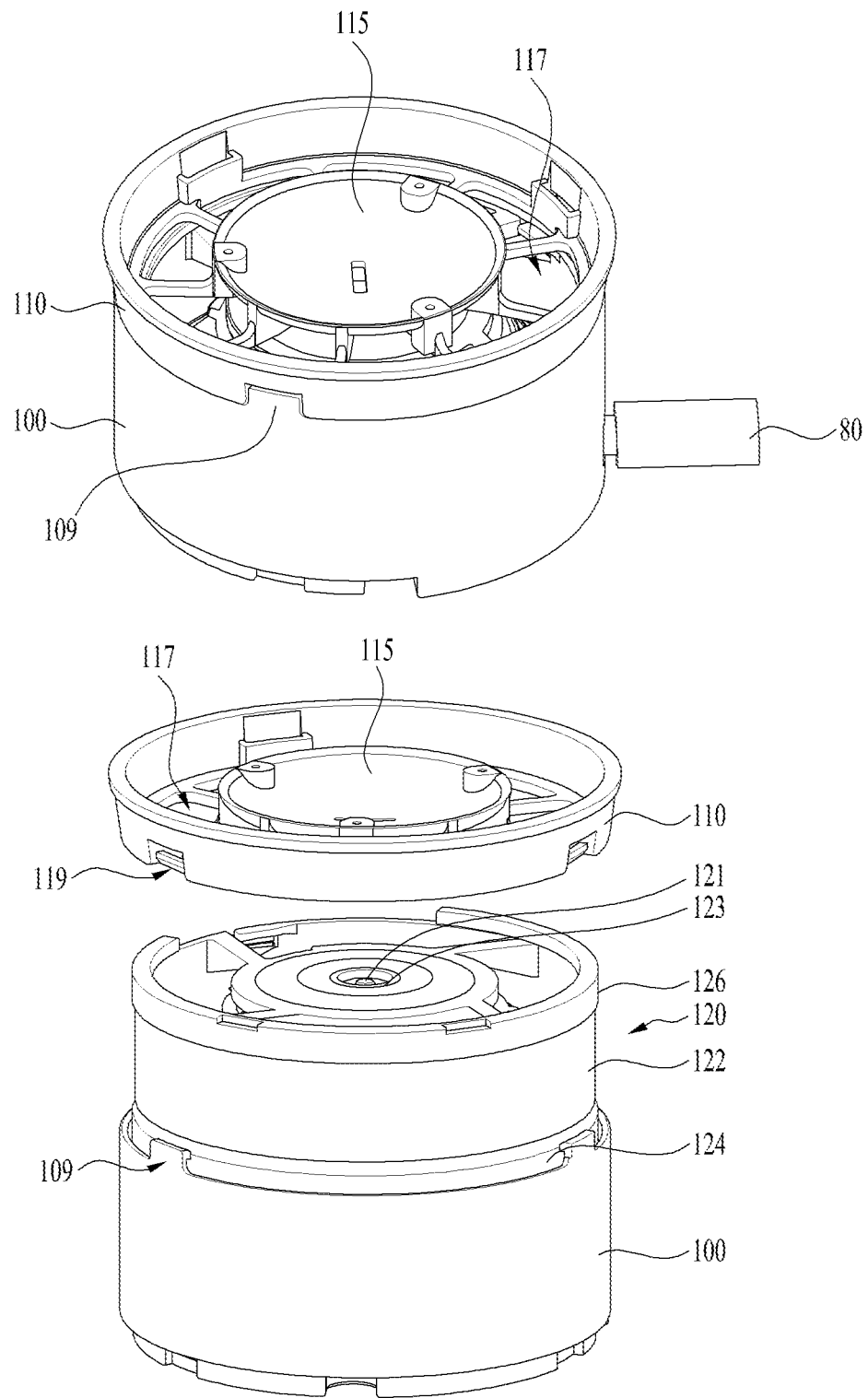
FIG. 5 is a diagram illustrating an exemplary blower.
Figure 6:
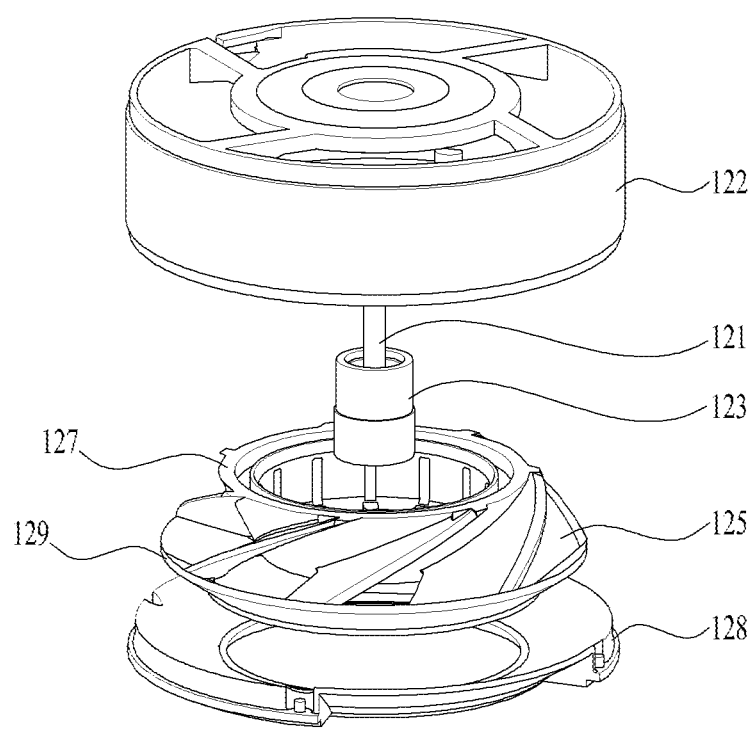
FIG. 6 is a diagram illustrating an internal configuration of an exemplary blower.

FIG. 5 is a diagram illustrating examples of the first housing 10 and the guide support frame 110, the blower 120, and FIG. 6 is a diagram illustrating an internal configuration of the blower 120.

Referring to FIGS. 4 to 6, the blower 120 can include a fan housing and a fan assembly accommodated in the fan housing.

The fan housing can include a main fan housing 122 that defines a structural frame of the fan housing, and a fan housing base 128 that supports the main fan housing 122 from the bottom. In some implementations, the fan housing can further include a lower fan housing coupling portion 124 disposed beneath the main fan housing 122 to couple the main fan housing 122 and the first housing 10 to each other, and an upper fan housing coupling portion 126 disposed on a top surface of the main fan housing 122 to couple the main fan housing 122 and the guide support frame 110 to each other.

The fan assembly can include a hollow hub 127, a shroud 129 spaced apart from the hub 127, and a blade 125 that connects the hub 127 and the shroud 129 to each other.

The hub 127, the blade 125, and the shroud 129 can be integrally provided and can rotate together. The shroud 129 can be disposed beneath the hub 127 and surround a portion of the hub 127. In some implementations, a diameter of the hub 127 can be less than a diameter of the shroud 129.

The blade 125 can include a plurality of blades, and extend from an outer circumferential surface of the hub 127 toward the shroud 129. In some implementations, the plurality of blades can be spaced apart from each other at equal spacings along a circumferential direction from the outer circumferential surface of the hub 127.

The plurality of blades can radially extend from the outer circumferential surface of the hub 127 to be connected to the shroud 129. In some implementations, each blade 125 can extend such that a position thereof is changed in a vertical direction, a left and right direction, and a front and rear direction.

The fan assembly can further include a driver 123 that rotates the hub 127, the blade 125, and the shroud 129, and a shaft 121 that can be rotated by the driver. In some implementations, when the driver 123 is provided as a motor, the driver 123 can include a stator that generates a rotating magnetic field, and a rotor that rotates by the magnetic field generated by the stator, and the shaft 121 can be coupled to the rotor.

The main fan housing 122 can accommodate the fan assembly from one side, and the fan housing base 128 can accommodate the fan assembly from the other side.

The fan housing base 128 can be coupled to the other end of the main fan housing 122 to rotatably support the fan assembly.

The shaft 121 and the driver 123 can be disposed in the fan housing. For example, the shaft 121 and the driver 123 can be disposed in at least one of the main fan housing 122 or the fan housing base 128.

Accordingly, the fan assembly may be rotatably disposed inside the fan housing.

However, when the fan housing is directly connected to the second frame 200, vibration or noise generated by the fan assembly is easily exposed to the outside. Therefore, in order to reduce the exposure of the vibration or the noise generated in the fan assembly to the outside, the fan housing can be fixed to the second frame 200 by a separate component.

In some implementations, the blower 120 can be accommodated in the first frame 100 and coupled to the second frame 200.

For example, the first frame 100 can fix the fan housing therein and can be coupled to an upper end of the second frame 200. That is, the first frame 100 can be coupled to the frame fastening portion 205 of the second frame 200.

The first frame 100 can have a height greater than a height in the vertical direction of the fan housing, so that even when the fan housing is coupled therein, the first frame 100 can have a free space beneath the fan housing. In some implementations, a USB PCB connectable to an USB 80 can be disposed in the free space.

Accordingly, the vibration or the noise generated in the fan assembly may not be directly transmitted to the second frame 200. As a result, an amount of vibration or noise generated in the fan assembly leaking to the outside can be reduced.

The guide support frame 110 on which the guide 55 that guides an operation of the flow converter 50 while coupling the fan housing is seated can be coupled to the upper portion of the first frame 100.

In some implementations, the first frame 100 and the guide support frame 110 can be coupled to each other in a hook scheme.

Hereinafter, the exemplary flow converter 50 will be described with reference to FIG. 7.

Figure 7:
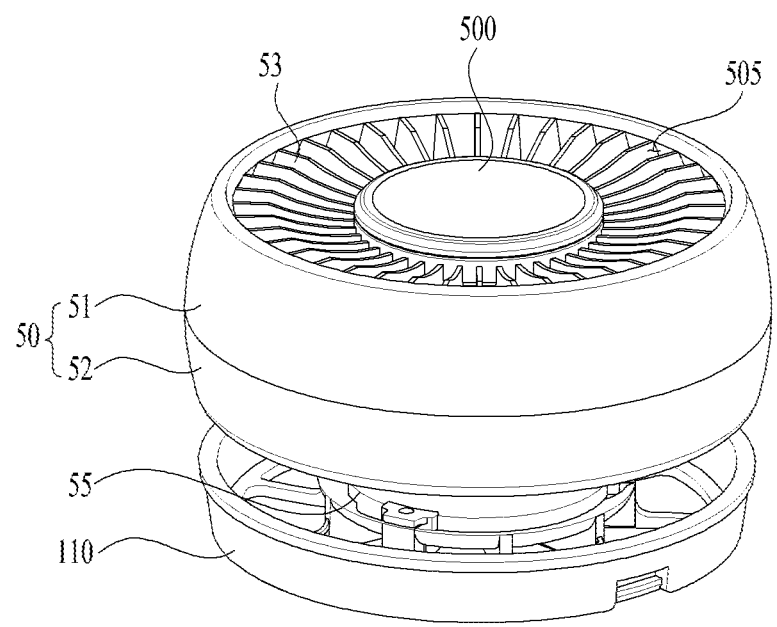
FIG. 7 is a diagram illustrating an exemplary flow converter.
Figure 7:
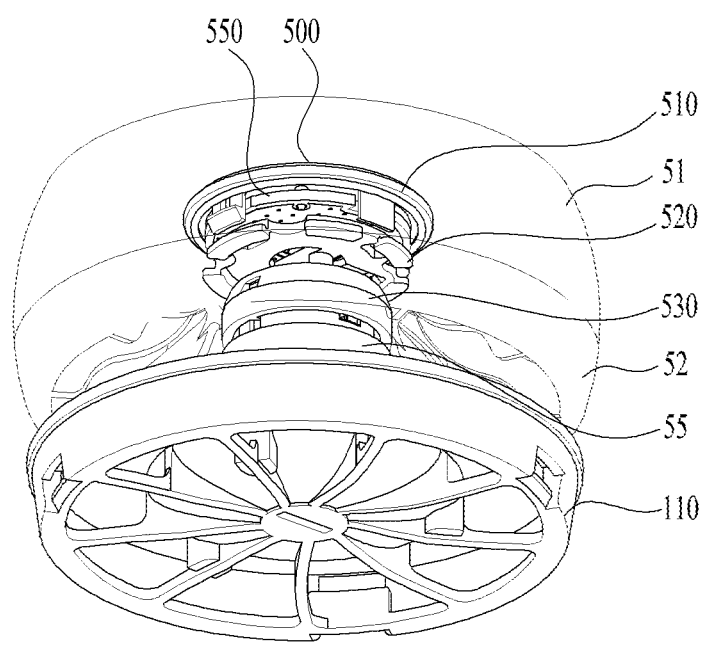

FIG. 7 is a diagram illustrating examples of the flow converter 50 and a view in which a discharge housing 51 and 52 is transparently shown.

Referring to FIG. 7, the guide 55 can be coupled to the guide support frame 110, and the flow converter 50 can be rotatably coupled to the guide 55.

For example, the flow converter 50 can include the discharge housing 51 and 52, a display 500 disposed in the middle of a top surface 501 of the discharge housing 51 and 52, and a discharge grill 53 disposed between the display 500 and the discharge housing 51 and 52. In some implementations, the display 500 can be a button 500 because the display 500 may also perform a role of a button.

The discharge housing 51 and 52 can include a guide coupling portion 530 disposed therein and rotatably coupled to the guide 55, a button PCB seating frame 520 disposed inside the discharge housing 51 and 52 and disposed on the guide coupling portion 530 to support a button PCB 710 from the bottom, and a button seating frame 510 disposed on the button PCB seating frame 520 to cover the button PCB 710 and to support the button 500 from the bottom.

In some implementations, the discharge housing 51 and 52 can include a first discharge housing 51 that defines an upper portion and a second discharge housing 52 that defines a lower portion.

The discharge housing 51 and 52 can be spaced apart from the guide support frame 110 by the guide 55. Accordingly, a space required for the discharge housing 51 and 52 to rotate can be defined between the flow converter 50 and the guide support frame 110. Accordingly, an interference between the discharge housing 51 and 52 interferes and the blower 120 can be blocked when the discharge housing 51 and 52 rotates.

The guide coupling portion 530 can be fixed to the guide 55 to rotate the discharge housing 51 and 52. The guide coupling portion 530 can rotate the discharge housing 51 and 52. For example, a ball and a ball joint can be used for the guide coupling portion 530. In some implementations, the discharge housing 51 and 52 can be rotated or moved at various angles with respect to the guide coupling portion 530.

Hereinafter, with reference to FIGS. 8 and 9, the sterilizer 300, the dust sensor assembly 330, and the battery 340 will be described.

Figure 9:
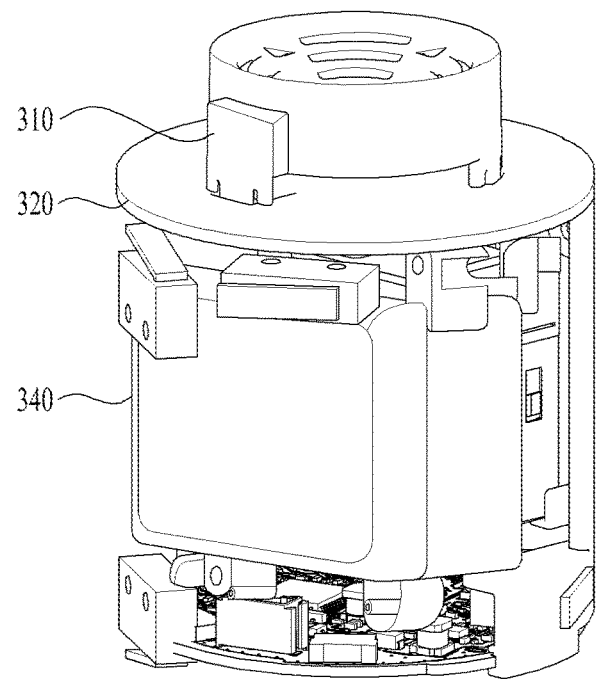
FIG. 9 is a diagram illustrating examples of a sterilizer, a dust sensor assembly, and a battery.
Figure 9:
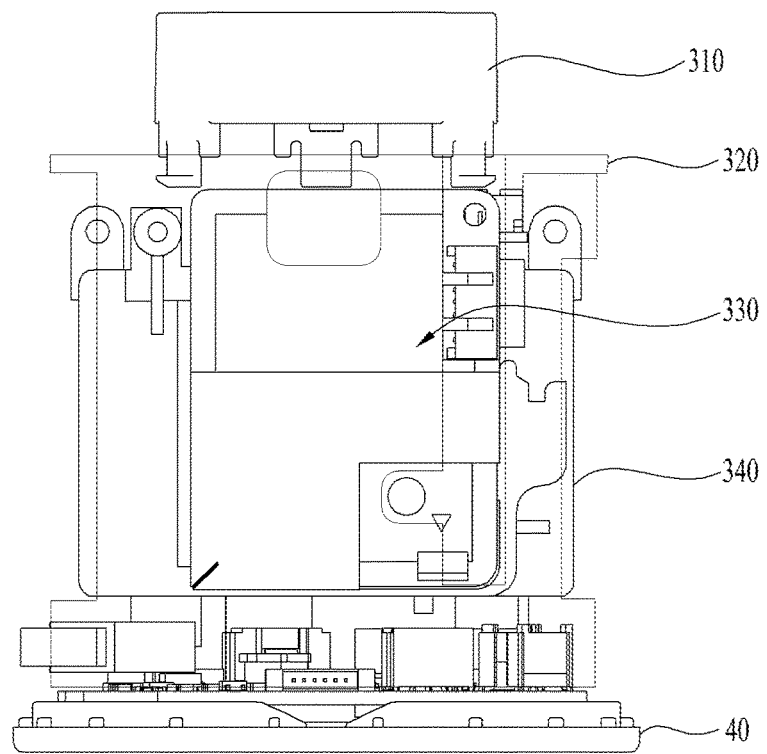

FIG. 9 is a diagram illustrating examples of the sterilizer 300, the dust sensor assembly 330, and the battery 340.

Referring to FIGS. 8 and 9, the sterilizer 300 can include a sterilizing light source 350 that generates sterilizing light, a first sterilizing casing 310 that accommodates the sterilizing light source 350 therein, and a second sterilizing casing 320 coupled to a lower portion of the first sterilizing casing 310 to support the first sterilizing casing 310 and the sterilizing light source 350.

The first sterilizing casing 310 can include a plurality of discharge portions defined to be fluid communication with an interior and an exterior of the first sterilizing casing 310. Accordingly, the air introduced through the suction portion 30 can flow into the first sterilizing casing 310 to perform cooling of the sterilizing light source 350. In some implementations, the sterilizing light generated from the sterilizing light source 350 can be emitted through the plurality of discharge portions.

The sterilizing light source 350 can include a sterilizing PCB and an irradiation portion mounted on the sterilizing PCB. The irradiation portion can be provided as a UVC LED.

The second sterilizing casing 320 can include a top surface frame coupled to the first sterilizing casing 310, a side surface frame extending downward from a circumference of the top surface frame, and a bottom surface frame connected to a lower end of the side frame and facing away from the top surface frame.

The dust sensor assembly accommodating portion and the battery accommodating portion can be disposed inside the second sterilizing casing 320. Accordingly, the dust sensor assembly 330 and the battery 340 can be accommodated in the second sterilizing casing 320 in the lower portion of the second frame 200.

The side frame of the second sterilizing casing 320 can further include an opening for inserting or withdrawing the dust sensor assembly 330 and the battery 340, or measuring a dust concentration of the air through the dust sensor assembly 330.

The dust sensor assembly 330 can include a dust sensor that measures the concentration of the dust and a fan that provides the airflow inside the second sterilizing casing 320.

The sterilizing light source 350 and the first sterilizing casing 310 can be accommodated together in the second upper frame 210 that defines the upper portion of the second frame 200, and the second sterilizing casing 320 can be accommodated in the second lower frame 220 that defines the lower portion of the second frame 200.

Hereinafter, an exemplary overall direction of the air flow and PCBs will be described with reference to FIG. 10.

Figure 10A:
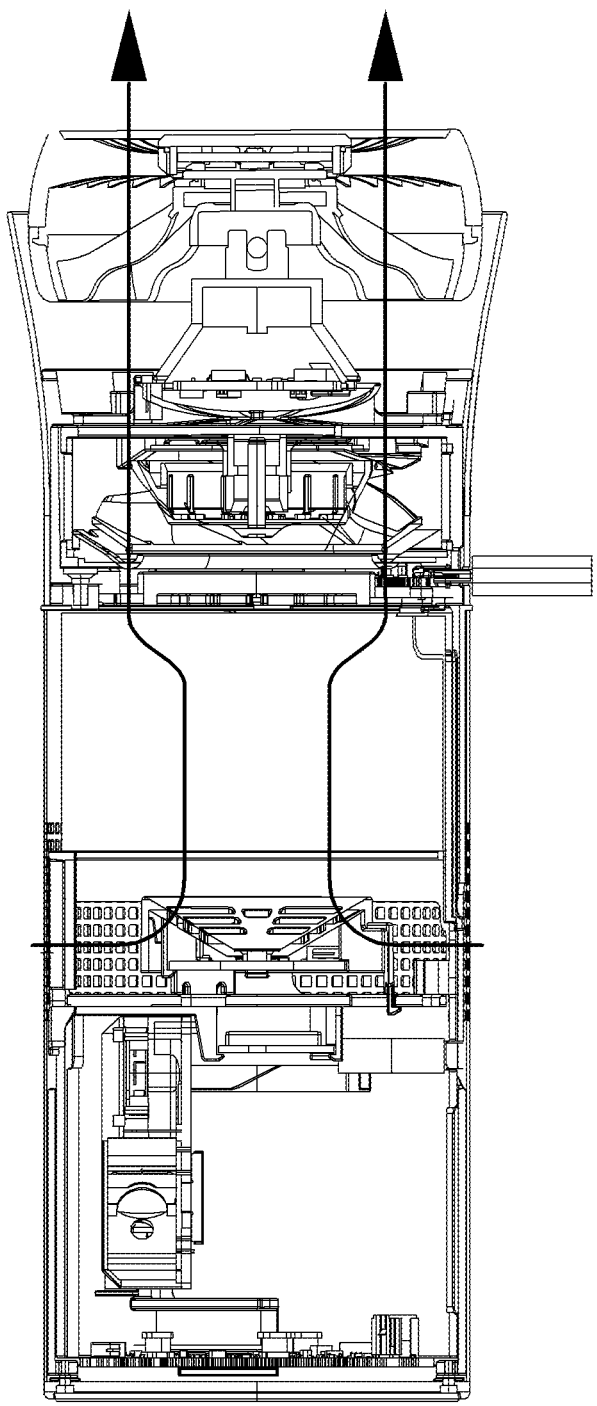
FIGS. 10A and 10B are diagrams illustrating a view of an airflow formed inside an exemplary air cleaner.
Figure 10B:
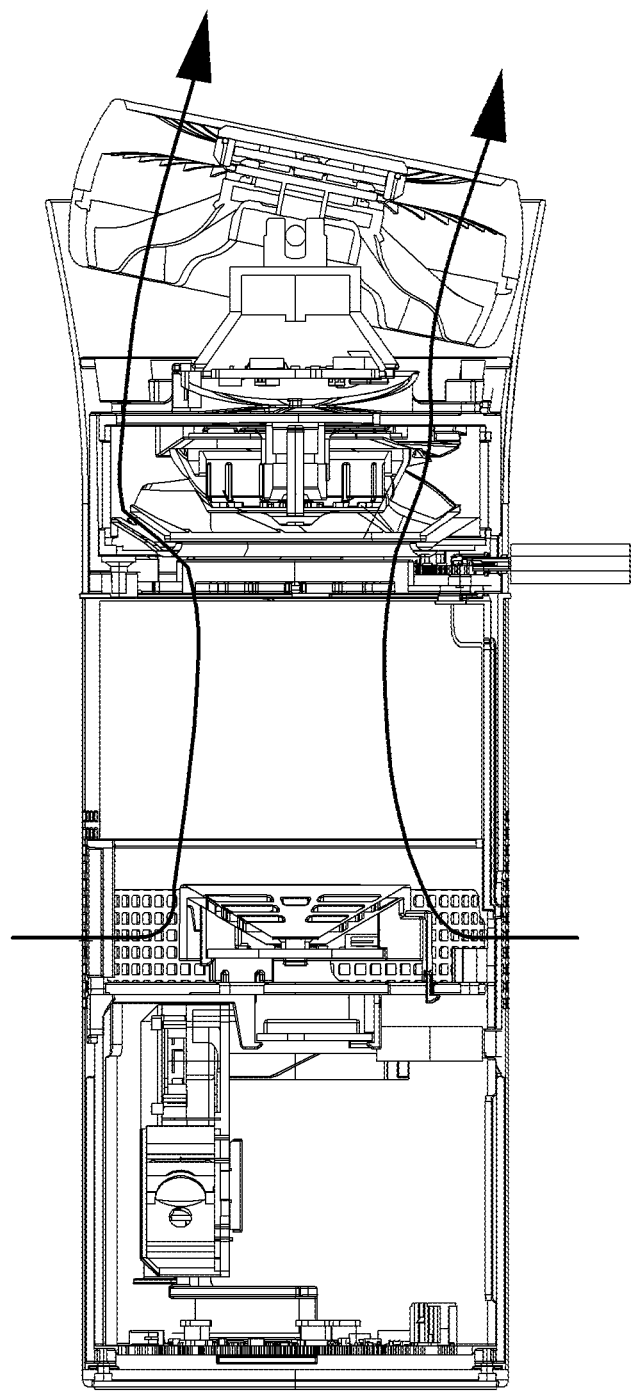

FIG. 10A is a diagram illustrating an example of an air flow in a state in which the flow converter 50 is not rotated, and FIG. 10B is a diagram illustrating an air flow in a state in which the flow converter 50 is rotated.

As described above, the suction portion 30 can be disposed to be spaced apart from the lower end of the second housing 20. Accordingly, the air located outside the housing 10 and 20 can flow into the housing 10 and 20 through the suction portion 30.

The air flowed into the housing 10 and 20 through the suction portion 30 can be sterilized by the sterilizer 300. In some implementations, the air flowing through the sterilizer 300 can flow upward after cooling the sterilizing PCB included in the sterilizing light source 350. For example, the air sterilized through the sterilizer 300 can flow toward the blower 120 within the housing 10 and 20. In some implementations, the foreign substances such as the dust can be removed from the air flowing toward the blower 120 by the filter assembly 250.

The air flowed through the blower 120 can flow upward toward the flow converter 50. In some implementations, a position of the discharge grill 53 can be changed depending on whether the flow converter 50 is moved, and the air passed through the blower 120 can flow toward the discharge grill 53 whose position is changed. Accordingly, the air introduced through the suction portion 30 can flow upward and be discharged to the outside through the discharge grill 53.

As described above, the air is introduced through the suction portion 30 and flows upward, so that the air does not pass through the battery 340. Therefore, it is possible to efficiently purify the air even by an airflow providing force of the blower 120 limited in the portable air cleaner 1.

In some implementations, the air cleaner 1 can further include a plurality of PCBs in addition to the sterilizing PCB.

For example, the button 500 that receives an input from the user can be disposed at an upper end of the flow converter 50. In some implementations, a button PCB that processes information input to the button 500 can be disposed below the button 500.

In some implementations, when a function such as displaying the information or lighting is added to the button 500, a display PCB that controls the display function can be further provided.

In some implementations, as described above with respect to FIG. 5, when the USB 80 is inserted into the air cleaner 1, a utility PCB that processes information input from the USB can be provided.

In some implementations, as described above with respect to FIG. 8, the sterilizing PCB for controlling the sterilizer 300 can be provided.

In some implementations, the battery 340 can have an electric PCB that supplies power to the above-described PCBs.

The button PCB, the display PCB, the utility PCB, the sterilizing PCB, and the electric PCB can be arranged from top to bottom in the order described.

The battery 340 can be connected to at least one of the above-described PCBs through a harness to supply the power.

In some examples, in the case of the display PCB, the utility PCB, the sterilizing PCB, and the electric PCB, disconnection of the harness is not a problem even when being directly connected to the battery 340. However, when the button PCB is directly connected to the battery 340, a position thereof is inevitably changed based on the movement of the flow converter 50, so that the disconnection of the harness may be a problem.

In order to solve the above problem, a scheme in which the power is supplied to the display PCB through the battery 340 and the button PCB is supplied with the power from the display PCB can be implemented.

Hereinafter, the exemplary sterilizer 300 will be described with reference to FIGS. 11 and 12.

Figure 11:
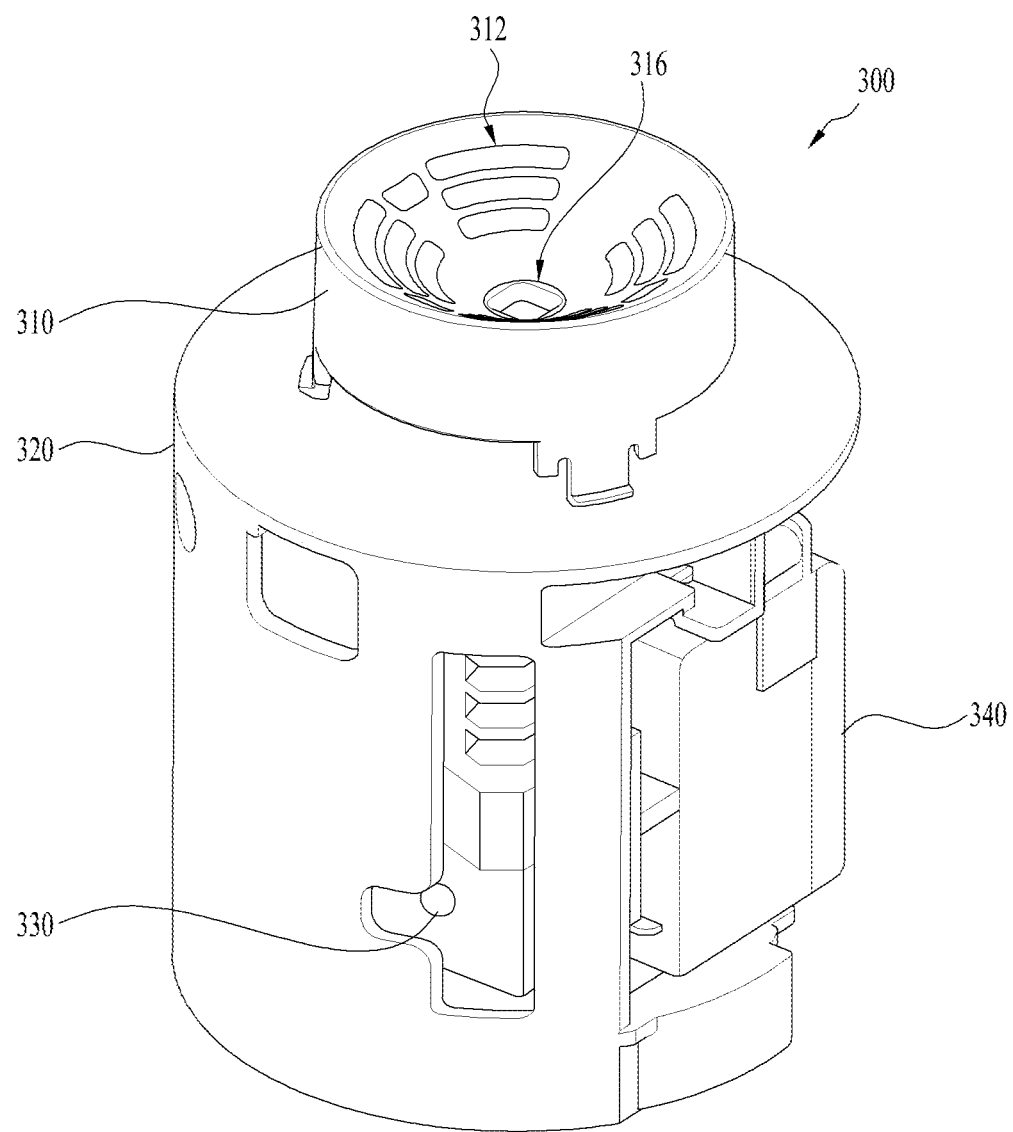
FIG. 11 is a diagram illustrating an exemplary sterilizer.
Figure 12:
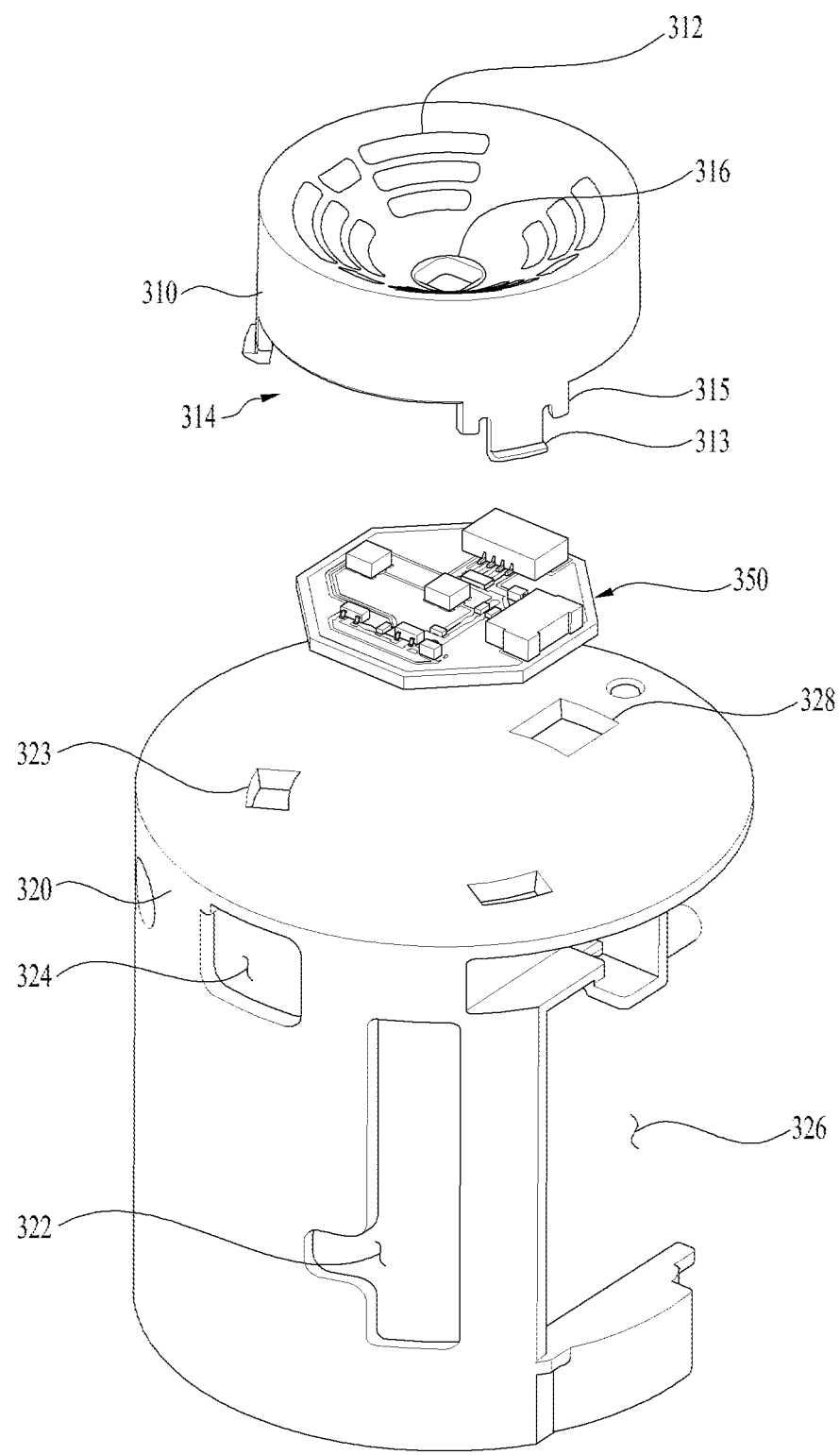
FIG. 12 is a diagram illustrating an exploded perspective view of the exemplary sterilizer of FIG. 11.

FIG. 11 is a diagram illustrating the exemplary sterilizer 300, and FIG. 12 is a diagram illustrating an exploded perspective view of the exemplary sterilizer 300.

Referring to FIGS. 11 and 12, the sterilizer 300 included in the air cleaner 1 can include the sterilizing light source 350 that generates the sterilizing light, and the sterilizing casing 310 and 320 that accommodates and supports the sterilizing light source 350, and the sterilizing casing can include the first sterilizing casing 310 that accommodates the sterilizing light source 350, and the second sterilizing casing 320 coupled to the lower portion of the first sterilizing casing 310 to support the first sterilizing casing 310 and the sterilizing light source 350.

The sterilizing light source 350 can include the sterilizing PCB, and the irradiation portion mounted on the sterilizing PCB, and the irradiation portion can be provided as the UVC LED.

The dust sensor assembly 330 and the battery 340 can be accommodated inside the second sterilizing casing. The dust sensor assembly 330 and the battery 340 can be detachably coupled to the second sterilizing casing 320, but the present disclosure is not necessarily limited thereto. For example, only one of the dust sensor assembly 330 or the battery 340 can be detachably coupled to the second sterilizing casing 320. Alternatively, each of the dust sensor assembly 330 and the battery 340 can be coupled to the second sterilizing casing 320 so as not to be detached therefrom.

In some implementations, a portion of the first sterilizing casing 310 can be spaced apart from the second sterilizing casing 320, so that the heat generated from the sterilizing light source 350 can be dissipated through a space between the at least a portion of the first sterilizing casing 310 and the second sterilizing casing 320.

The sterilizing casing 310 and 320 can include the plurality of discharge portions. The sterilizing light generated from the sterilizing light source 350 can be irradiated through the plurality of discharge portions, and the heat generated from the sterilizing light source 350 can be dissipated through the plurality of discharge portions. For example, at least one of the plurality of discharge portions can be defined to be in fluid communication with the suction portion 30 of the housing 10 and 20 at a position between the first sterilizing casing 310 and the second sterilizing casing 320, and can serve as a heat dissipating portion for dissipating the heat generated from the sterilizing light source 350.

For example, the sterilizer 300 can further include a main discharge portion 316 that defines an opening at a central portion of a top surface of the first sterilizing casing 310 and to which the sterilizing light generated by the sterilizing light source 350 is irradiated, a first discharge portion 312 that defines one or more opening at the top surface of the first sterilizing casing 310 to dissipate the heat generated from the sterilizing light source 350, and a second discharge portion 314 that defines an opening at a sidewall of the first sterilizing casing 310 to dissipate the heat generated from the sterilizing light source 350.

In some implementations, the sterilizing light generated by the sterilizing light source 350 can be irradiated through the first discharge portion 312 and/or the second discharge portion 314 in addition to the main discharge portion 316. However, UVC light generated through the UVC LED included in the sterilizing light source 350 may be harmful to a human body, so that it is necessary to block the UVC LED from leaking directly to the outside of the housing 10 and 20.

In some implementations, a portion of the suction portion 30 can be disposed at a position to overlap with the second discharge portion 314, and the suction portion 30 and the second discharge portion 314 can be disposed to be in fluid communication with each other. In some implementations, the suction portion 30 can be disposed at a position not overlapping with the first discharge portion 312, and thus, the suction portion 30 and the first discharge portion 312 can be disposed so as not to be in fluid communication with each other. However, because a separate blocking member such as a partition is not disposed between the suction portion 30 and the first discharge portion 312, the suction portion 30 and the first discharge portion 312 may be indirectly in fluid communication with each other.

Hereinafter, the sterilizing light and a heat dissipating structure of the exemplary sterilizing light source 350 will be described with reference to FIGS. 11, 12, 13A and B, and 14 together.

Figure 13A:
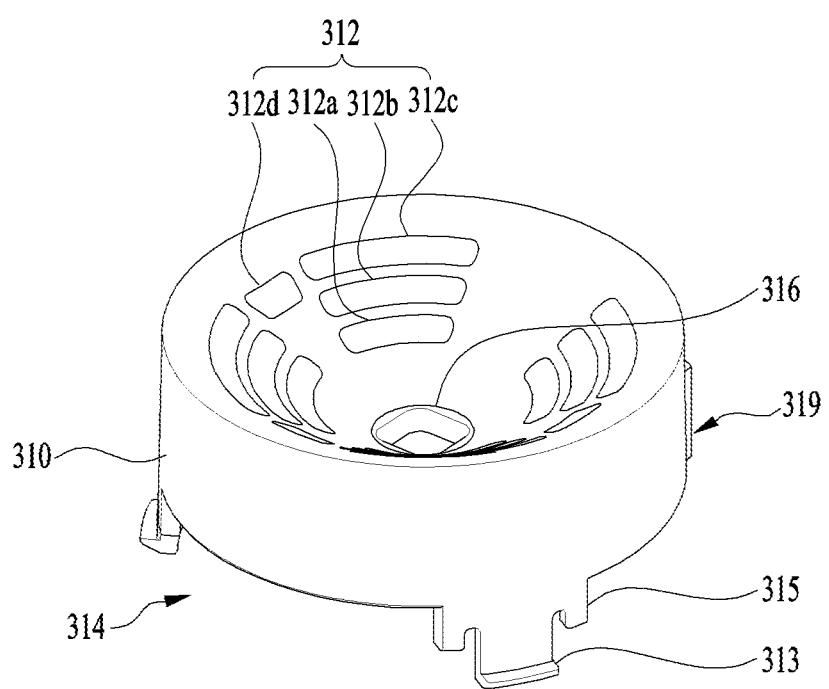
FIGS. 13A and 13B are diagrams illustrating an exemplary first sterilizing casing.
Figure 13B:
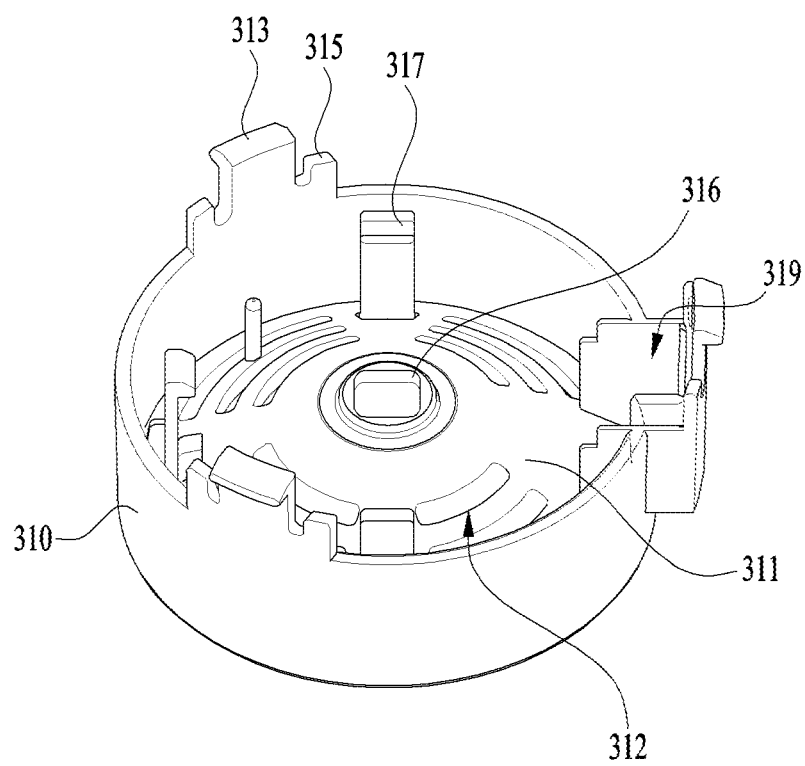
Figure 14:
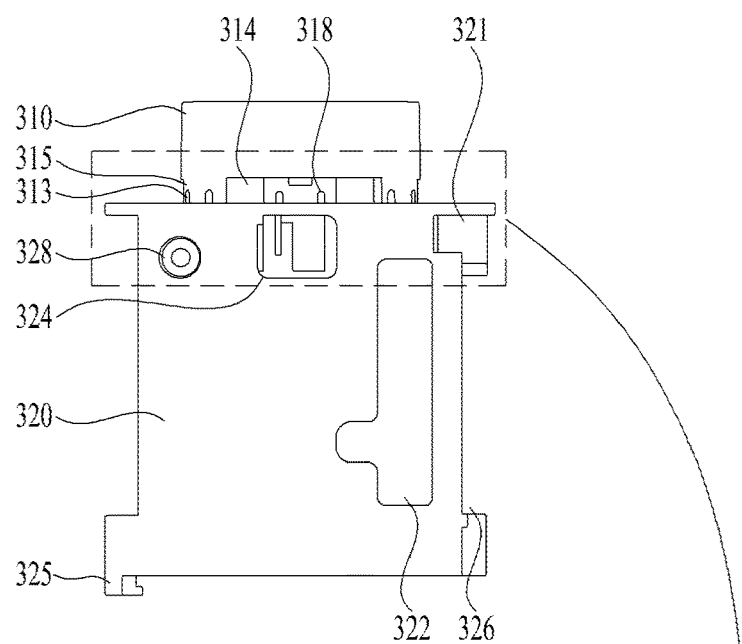
FIG. 14 is a diagram illustrating a side view of an exemplary coupling structure of a first sterilizing casing and a second sterilizing casing.
Figure 14:
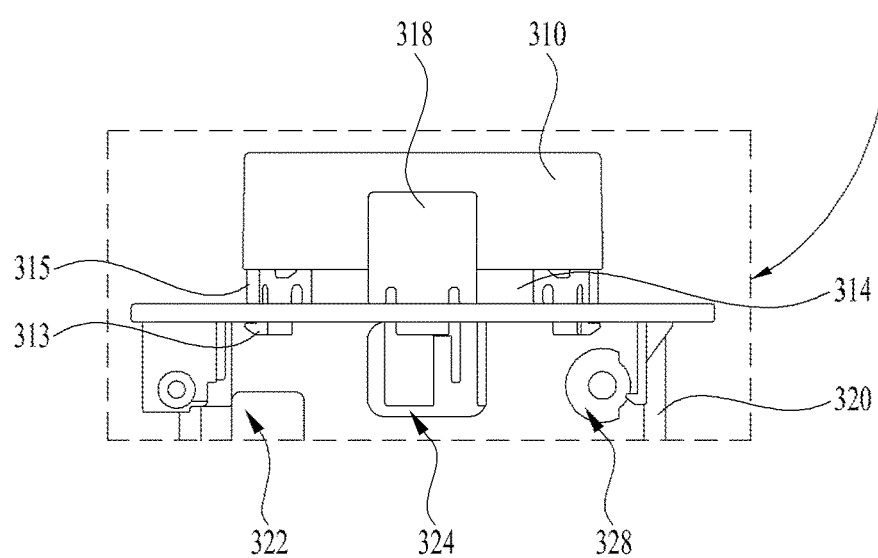

FIGS. 13A and B are diagrams illustrating an upper perspective view and a lower perspective view of the exemplary first sterilizing casing 310, respectively, FIG. 14 is a diagram illustrating side views of an exemplary coupling structure of the first sterilizing casing 310 and the second sterilizing casing 320.

Referring to FIGS. 11, 12, 13A and B, and 14 together, the first sterilizing casing 310 can include a protrusion protruding from a sidewall of the first sterilizing casing 310 toward the second sterilizing casing 320, the second sterilizing casing 320 can include a coupling groove 323 and 328 defined at a position corresponding to the protrusion, and the first sterilizing casing 310 and the second sterilizing casing 320 can be coupled to each other by fastening between the protrusion and the coupling groove 323 and 328.

In some implementations, the protrusion and the coupling groove 323 and 328 can include a plurality of protrusions and a plurality of coupling grooves, respectively. In some implementations, the number of plurality of protrusions and the number of plurality of coupling grooves may be the same.

In some implementations, the protrusion can include a first protrusion 313 and a second protrusion 315, and the first protrusion 313 and the second protrusion 315 can have different extension lengths. For example, the extension length can be an extension length in the vertical direction, that is, in a direction from the sidewall of the first sterilizing casing 310 toward a top surface of the second sterilizing casing 320.

An extension length of the first protrusion 313 can be greater than an extension length of the second protrusion 315, and each second protrusion 315 can be disposed on each of both sides of the first protrusion 313. For example, two second protrusions 315 can be respectively disposed on both sides of one first protrusion 313 along a circumferential direction of the first sterilizing casing 310.

The first protrusion 313 can pass through the coupling groove 323 and 328 to be fastened to each other, and the second protrusion 315 can contact a portion adjacent to the coupling groove 323 and 328 of the top surface of the second sterilizing casing 320 without passing through the coupling groove 323 and 328. Accordingly, the second discharge portion 314 can be defined between the sidewall of the first sterilizing casing 310 and the top surface of the second sterilizing casing 320, and the heat generated from the sterilizing light source 350 can be dissipated through the second discharge portion 314.

The sterilizer 300 can further include a third discharge portion 318 defined at a position between the first protrusion 313 and the second protrusion 315 to be recessed in a direction away from the top surface of the second sterilizing casing 320 to dissipate the heat generated from the sterilizing light source 350. Accordingly, the third discharge portion 318 can be further provided between the sidewall of the first sterilizing casing 310 and the top surface of the second sterilizing casing 320, and the heat generated from the sterilizing light source 350 can be dissipated through the third discharge portion 318.

For example, in addition to the first discharge portion 312 that defines an opening at the top surface of the first sterilizing casing 310 to dissipate the heat generated from the sterilizing light source 350, the sterilizer 300 can further include the second discharge portion 314 and the third discharge portion 318 that defines an opening at the sidewall of the first sterilizing casing 310 to dissipate the heat generated from the sterilizing light source 350, so that the heat generated from the sterilizing light source 350 can be effectively dissipated in many directions.

In some implementations, the first discharge portion 312 may have a main purpose of irradiating the sterilizing light generated from the sterilizing light source 350 rather than dissipating the heat generated from the sterilizing light source 350 together with the main discharge portion 316. On the other hand, the second discharge portion 314 and the third discharge portion 318 may have a main purpose of dissipating the heat generated from the sterilizing light source 350 rather than irradiating the sterilizing light generated from the sterilizing light source 350. Accordingly, the main discharge portion 316 and the first discharge portion 312 may together refer to a light irradiation portion, and the second discharge portion 314 and the third discharge portion 318 may together refer to a heat dissipating portion.

In some implementations, the top surface of the first sterilizing casing 310 can have a shape in which a center portion thereof is concave compared to an edge portion thereof. For example, the top surface of the first sterilizing casing 310 can have a downward slope ward the top surface of the second sterilizing casing 320 from the edge portion to the center portion.

In some implementations, the first discharge portion 312 can include a plurality of through-holes 312a, 312b, 312c, and 312d having different extension lengths extending in a circumferential direction of the top surface of the first sterilizing casing 310.

In some implementations, the first discharge portion 312 can include a first through-hole 312a, a second through-hole 312b, and a third through-hole 312c, and extension lengths of the first through-hole 312a, the second through-hole 312b, and the third through-hole 312c extending in the circumferential direction of the first sterilizing casing can gradually increase in this order. In some implementations, the first discharge portion 312 can further include a fourth through-hole 312d having an extension length less than an extension length of the first through-hole 312a. Each of the first through-hole 312a, the second through-hole 312b, the third through-hole 312c, and the fourth through-hole 312d can include a plurality of through-holes.

In some implementations, the fourth through-hole 312d can be defined between two third through-holes 312c adjacent to each other or between two second through-holes 312b adjacent to each other, but the present disclosure is not necessarily limited thereto. For example, the fourth through-hole 312d can be defined between two first through-holes 312a adjacent to each other.

As the first to third through-holes 312a to 312c are defined in the non-flat top surface of the first sterilizing casing 310, when the sterilizing light generated from the sterilizing light source 350 is irradiated through the first discharge portion 312, the sterilizing light can be irradiated in a non-vertical, inclined direction, for example, in a direction toward a central shaft of the sterilizer 300. Accordingly, a light leakage phenomenon in which the sterilizing light irradiated from the sterilizer 300 leaks to the outside can be blocked.

The protrusion can further include a third protrusion 317 extending from the top surface of the first sterilizing casing 310 toward the top surface of the second sterilizing casing 320 and protruding in the vertical direction, and the first sterilizing casing 310 and the sterilizing light source 350 can be coupled to each other by the third protrusion 317.

In some implementations, the battery 340 for supplying the power can be accommodated inside the second sterilizing casing 320. For example, the battery 340 and the sterilizing light source 350 can be electrically connected to each other by the harness.

In some implementations, the dust sensor assembly 330 that measures the dust in the air can be further accommodated inside the second sterilizing casing 320, and the battery 340 and the dust sensor assembly 330 can also be electrically connected to each other by the harness. The dust sensor assembly 330 can include the dust sensor that measures the concentration of the dust in the air and the fan capable of providing the airflow inside the second sterilizing casing 320.

In some implementations, at least one coupling groove 328 of the plurality of coupling grooves 323 and 328 can be defined to have a larger area than other coupling grooves 323 to provide a space in which the harness extends. The harness can extend through the at least one coupling groove 328. In some implementations, the at least one coupling groove 328 may be a component that allows the first sterilizing casing 310 and the second sterilizing casing 320 to be coupled, and may be a component that provides a movement path of the harness that electrically connects the sterilizing light source 350 accommodated in the first sterilizing casing 310 with the battery 340 accommodated in the second sterilizing casing 320. Therefore, hereinafter, a coupling groove not penetrated by the harness among the plurality of coupling grooves 323 and 328 may refer to a first coupling groove 323, and a coupling groove penetrated by the harness among the plurality of coupling grooves 323 and 328 may refer to a second coupling groove 328.

In some implementations, a protrusion 319 corresponding to the second coupling groove 328 among the plurality of protrusions can protrude farther in the circumferential direction of the first sterilizing casing 310 than other protrusions. For example, the protrusion 319 corresponding to the second coupling groove 328 may be a component providing the movement path of the harness, and may refer to a fourth protrusion 319.

The second sterilizing casing 320 can include a dust sensor inlet 322 that defines an opening at the sidewall of the second sterilizing casing 320 to introduce the air into the second sterilizing casing 320, and a dust sensor discharge portion 324 that defines an opening at the sidewall of the second sterilizing casing 320 to discharge the air inside the second sterilizing casing 320. Therefore, when the fan included in the dust sensor assembly 330 provides the airflow, after the air is introduced through the dust sensor inlet 322, the concentration of dust in the introduced air can be measured by the dust sensor, and then the air from which the concentration of dust is measured can be discharged through the dust sensor discharge portion 324.

The second sterilizing casing 320 can further include a dust sensor exposing portion 327 that defines an opening at the sidewall of the second sterilizing casing 320 to remove the dust accumulated in the dust sensor.

Hereinafter, an exemplary arrangement structure in the second frame 200 of the sterilizer 300 will be described with reference to FIG. 15.

Figure 15:
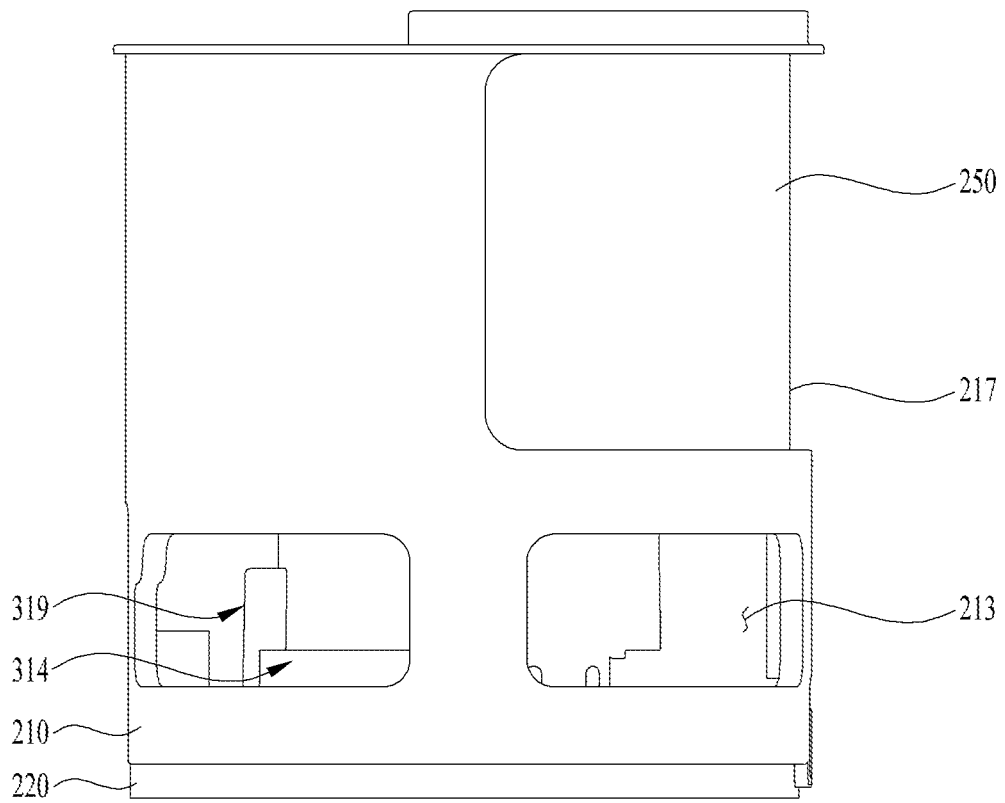
FIG. 15 is a diagram illustrating a side view of a sterilizer, a filter assembly, and a second frame.

FIG. 15 is a diagram illustrating a side view of examples of the sterilizer 300, the filter assembly 250, and the second frame 200.

Referring to FIG. 15, the second upper frame 210 can include the air inlet 213 that defines an opening at the sidewall of the second upper frame 210 and that is in fluid communication with the suction portion 30. The suction portion 30, the air inlet 213, and the second discharge portion 314 may be in fluid communication with each other.

Therefore, the heat dissipated from the sterilizing light source 350 can be dissipated into the second frame 200 through the second discharge portion 314 and then dissipated to the outside through the air inlet 213 and the suction portion 30 in turn.

As described above, according to the air cleaner 1, at least one discharge portion 314 of the plurality of discharge portions 312, 314, 316, and 318 included in the sterilizer 300 may be in fluid communication with the suction portion 30 included in the housing 10 and 20. Accordingly, the heat generated when irradiating the sterilizing light may be effectively dissipated to the outside.

In addition, the first sterilizing casing 310 included in the sterilizer 300 can have the non-flat top surface. Accordingly, the light leakage phenomenon in which the sterilizing light generated from the sterilizing light source 350 accommodated in the first sterilizing casing 310 leaks to the outside can be blocked.

What is claimed is:

1. An air cleaner comprising:
a housing including a suction portion configured to suction air from an outside of the housing and a discharge portion configured to discharge air from the housing;
a frame disposed inside the housing;
a sterilizer disposed inside the frame and configured to sterilize the suctioned air;
a filter assembly disposed in the frame and configured to filter air inside the housing;
a blower disposed inside the frame and configured to move air inside the housing;
a flow converter that is disposed on a top surface of the housing and that is configured to guide a flow of air inside the housing and discharge air inside the housing to an outside of the housing; and
a guide configured to guide a direction of the flow converter,
wherein the sterilizer includes:
a sterilizing light source configured to generate sterilizing light,
a first sterilizing casing configured to accommodate the sterilizing light source, and
a second sterilizing casing that is coupled to a lower portion of the first sterilizing casing and that supports the first sterilizing casing and the sterilizing light source, and wherein a portion of the first sterilizing casing is spaced apart from the second sterilizing casing to define a space therebetween that is configured to dissipate heat generated from the sterilizing light source.

2. The air cleaner of claim 1, wherein the sterilizer further includes:
a main discharge portion that defines an opening at a central portion of a top surface of the first sterilizing casing to irradiate the sterilizing light generated by the sterilizing light source,
a first discharge portion that defines an opening at the top surface of the first sterilizing casing to dissipate the heat generated from the sterilizing light source, and
a second discharge portion that defines an opening at a sidewall of the first sterilizing casing to dissipate the heat generated from the sterilizing light source.

3. The air cleaner of claim 2, wherein a portion of the suction portion overlaps the second discharge portion.

4. The air cleaner of claim 3, wherein the frame includes an air inlet that defines an opening at a sidewall of the frame and that is in fluid communication with the suction portion, and
wherein the suction portion, the air inlet, and the second discharge portion are in fluid communication with each other.

5. The air cleaner of claim 2, wherein the first sterilizing casing includes a protrusion protruding from the sidewall of the first sterilizing casing toward the second sterilizing casing,
wherein the second sterilizing casing includes a coupling groove defined at a position corresponding to the protrusion, and
wherein the first sterilizing casing and the second sterilizing casing are coupled to each other by fastening between the protrusion and the coupling groove.

6. The air cleaner of claim 5, wherein the protrusion and the coupling groove include a plurality of protrusions and a plurality of coupling grooves, respectively, and
wherein a number of the plurality of protrusions is equal to a number of the plurality of coupling grooves.

7. The air cleaner of claim 5, wherein the protrusion includes a first protrusion that includes a first set of protrusions and a second protrusion that includes a second set of protrusions, and
wherein the first protrusion and the second protrusion have different extension lengths.

8. The air cleaner of claim 7, wherein an extension length of the first protrusion is greater than an extension length of the second protrusion, and
wherein each of the second set of protrusions is disposed on each of both sides of the first set of protrusions, respectively.

9. The air cleaner of claim 7, wherein the protrusion further includes a third protrusion protruding from the top surface of the first sterilizing casing toward the second sterilizing casing, and
wherein the first sterilizing casing and the sterilizing light source are coupled to each other by the third protrusion.

10. The air cleaner of claim 7, wherein the first protrusion passes through the coupling groove to couple the coupling groove, and
wherein the second protrusion is in contact with a portion of a top surface of the second sterilizing casing adjacent to the coupling groove.

11. The air cleaner of claim 7, wherein the sterilizer further includes a third discharge portion that is disposed between the first protrusion and the second protrusion and that recesses in a direction away from the second sterilizing casing to dissipate the heat generated from the sterilizing light source.

12. The air cleaner of claim 6, further comprising a battery that is disposed inside the second sterilizing casing and that is configured to supply power,
wherein the sterilizing light source and the battery are electrically connected to each other by a harness.

13. The air cleaner of claim 12, wherein one of the plurality of coupling grooves has an area greater than an area of each of the remaining coupling grooves, and
wherein the harness extends through the at least one coupling groove.

14. The air cleaner of claim 13, wherein a protrusion corresponding to the at least one coupling groove among the plurality of protrusions protrudes farther in a circumferential direction of the first sterilizing casing than the remaining protrusions.

15. The air cleaner of claim 2, wherein the top surface of the first sterilizing casing has a concave shape.

16. The air cleaner of claim 15, wherein the top surface of the first sterilizing casing has a downward slope toward a top surface of the second sterilizing casing from an edge portion to the central portion of the top surface of the first sterilizing casing.

17. The air cleaner of claim 16, wherein the first discharge portion includes a plurality of through-holes having different extension lengths extending in a circumferential direction of the top surface of the first sterilizing casing.

18. The air cleaner of claim 17, wherein the first discharge portion includes a first through-hole, a second through-hole, and a third through-hole, and
wherein an extension length of the third through-hole is greater than an extension length of the second through-hole, and the extension length of the second through-hole is greater than an extension length of the first through-hole, the extension length of each of the first through-hole, the second through-hole, and the third through-hole extending in the circumferential direction of the top surface of the first sterilizing casing.

19. The air cleaner of claim 18, wherein the first discharge portion further includes a fourth through-hole having an extension length less than the first through-hole.

20. The air cleaner of claim 19, wherein each of the first through-hole, the second through-hole, the third through-hole, and the fourth through-hole includes a plurality of through-holes.

* * * * *